United States Patent
Wang et al.

(10) Patent No.: US 11,359,250 B2
(45) Date of Patent: Jun. 14, 2022

(54) METHODS OF DETECTING TRICHOMONAS VAGINALIS

(71) Applicant: Cepheid, Sunnyvale, CA (US)

(72) Inventors: James Wang, Sunnyvale, CA (US); Sudhir Alugupally, Fremont, CA (US); Rosa Yu, Sunnyvale, CA (US); Sally Yousif, San Diego, CA (US)

(73) Assignee: CEPHEID, Sunnyvale, CA (US)

( * ) Notice: Subject to any disclaimer, the term of this patent is extended or adjusted under 35 U.S.C. 154(b) by 0 days.

(21) Appl. No.: 16/255,883

(22) Filed: Jan. 24, 2019

(65) Prior Publication Data

US 2019/0249264 A1 Aug. 15, 2019

Related U.S. Application Data

(62) Division of application No. 15/325,356, filed as application No. PCT/US2014/046653 on Jul. 15, 2014, now Pat. No. 10,233,506.

(51) Int. Cl.
 *C12Q 1/6893* (2018.01)

(52) U.S. Cl.
 CPC ..... *C12Q 1/6893* (2013.01); *C12Q 2600/158* (2013.01); *G01N 2333/44* (2013.01)

(58) Field of Classification Search
 None
 See application file for complete search history.

(56) References Cited

U.S. PATENT DOCUMENTS

| 6,582,908 B2 | 6/2003 | Fodor et al. |
| 6,773,882 B2 | 8/2004 | Hogan et al. |

FOREIGN PATENT DOCUMENTS

| CN | 102719529 A | 10/2012 |
| WO | 2005031005 A2 | 4/2005 |
| WO | 2010083274 A1 | 7/2010 |
| WO | 2012075321 A2 | 6/2012 |

OTHER PUBLICATIONS

Dieffenbach et al., "General Concepts for PCR Primer Design," PCR Methods Appl., 3: 30-37 (1993).
International Search Report and Written Opinion of International Application No. PCT/US2014/046653 dated Sep. 24, 2014 (12 pages).
Jordan et al., "Taqman-Based Detection of Trichomonas vaginalis DNA from Female Genital Specimens," J.Clin. Micrbiol., vol. 39, No. 11, p. 3819-3822 (Nov. 2001).
Roux, K.H., Optimization and troubleshooting in PCR, PCR Methods Appl., 4: 185-194 (1995).
Smith et al., "Novel Core Promoter Elements and a Cognate Transcription Factor in the Divergent Unicellular Eukaryote Trichomonas Vaginalis," Moleculer and Cellular Biology, vol. 31, No. 7, pp. 1444-1458 (Jan. 18, 2011).
"Trichomaonas vaginalis G3 40S ribosomal protein S23, putative (TVAG_249090) partial mRNA NCBI Reference Sequence: XM_001582785.1", GenBank, p. 1 (Nov. 2, 2008).
"Trichomonas vaginalis G3 40S ribosomal protein S23, putative (TVAG_109730) partial mRNA NCBI Reference Sequence: XM_001322577.1", GenBank, p. 1 (Nov. 2, 2008).
Carlton et al., "Draft Genome Sequences of the Sexually Transmitted Pathogen Trichomonas vaginalis", Science, 315(5809): 207-212 (Jan. 12, 2007) (15 pages).

*Primary Examiner* — Katherine D Salmon
(74) *Attorney, Agent, or Firm* — McNeill Baur PLLC

(57) ABSTRACT

Compositions and methods for detecting *Trichomonas vaginalis* are provided.

21 Claims, No Drawings
Specification includes a Sequence Listing.

SEQUENCE LISTING

<160> NUMBER OF SEQ ID NOS: 10

<210> SEQ ID NO 1
<211> LENGTH: 26
<212> TYPE: DNA
<213> ORGANISM: Artificial Sequence
<220> FEATURE:
<223> OTHER INFORMATION: Synthetic

<400> SEQUENCE: 1

```
gtaacaacct tggagttctt cttaag                                            26

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
acatcaatct acaagacacc acttga                                            26

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
agtttggctg cttagcttcg ac                                                22

<210> SEQ ID NO 4
<211> LENGTH: 508
<212> TYPE: DNA
<213> ORGANISM: Trichomonas vaginalis

<400> SEQUENCE: 4
ggccggcctt tctgatgggt aagtctaaag cttgcggtcg tctcgctgct cgtaaactcc       60
gtcttgcaca caagtccaac ttgtgggctt ccaacgcata ccgccgttcc cttggtacat      120
caatctacaa gacaccactt gagggtacat caatggcatc tggcatcgtc gtcggcaagg      180
tcgctgtcga agccaagcag ccaaaactct gctattcgta aagctgtccgt gttcagctta     240 agaagaactc taaggttgtc acagctttcg ttccacgcga tggttccctc cgtcttattg      300
atgataacga ccgtgttctt attgccggta tgggtcgttc tggccgttct gtcggtgacc      360
ttccaggatg ccgtttcaaa gttatcaagg tcgctggttt ctccctcctt gctctttggc      420
tcggcaagaa ggagaagccg cgcagctaaa taaatactct gggtttacc ggtaaataaa       480 aacatatatt acgaaataca aatattat                                        508

<210> SEQ ID NO 5
<211> LENGTH: 146
<212> TYPE: DNA
<213> ORGANISM: Artificial Sequence
<220> FEATURE:
<223> OTHER INFORMATION: Synthetic

<400> SEQUENCE: 5
acatcaatct acaagacacc acttgaaggc acctcaatgg cctccggcat tgttgtcggc       60
aaagttgctg tcgaagctaa gcagccaaac tccgctattc gtaaagcagt tcgtgttcag      120
cttaagaaga actctaaagt tgttac                                          146

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
```

```
gagttcttct taagctgaac ac                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
gagttcttct tgagctgaac ac                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
aacaaccttg gagttcttct ta                                              22

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
atctacaaga caccacttga                                                 20

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
agtttggctg cttggcttcg ac                                              22
```

METHODS OF DETECTING TRICHOMONAS VAGINALIS

1. FIELD OF THE INVENTION

Compositions and methods for detecting *Trichomonas vaginalis* are provided.

2. BACKGROUND

The protozoan *Trichomonas vaginalis* is responsible for trichomoniasis, which is a common sexually transmitted infection that can infect both men and women. There are 7.4 million cases of trichomoniasis annually in the United States. Trichomoniasis infections can be symptomatic or asymptomatic. See, e.g., Ginocchio et al., *J. Clin. Microbiol.* 2012, 50: 2601-2608. In women, trichomoniasis is one of a range of conditions that comprise vaginal discharge. See, e.g., Centers for Disease Control and Prevention (CDC). CDC fact sheet: trichomoniasis. 2010. www.cdc.gov/std/trichomonas/STDFact-Trichomoniasis.htm. Symptoms in females can include itching, burning, redness, or soreness of the genitals, unusual odor, discomfort with urination, or a thin clear, white, yellow, or green discharge. See id. In men, trichomoniasis may cause non-gonococcal urethritis (NGU). Symptoms in males can include itching or burning inside the penis, burning after ejaculation or urination, or penile discharge. See, e.g, Workowski et al., Centers for Disease Control and Prevention. Sexually transmitted disease treatment guidelines, 2010. MMWR 2010; 59 (RR-12):1-110; Centers for Disease Control and Prevention. Biosafety in Microbiological and Biomedical laboratories. www.cdc.gov/biosafety/publications/.

Improved methods for detection of *Trichomonas vaginalis* (TV) are needed. In particular, a highly specific, accurate, and sensitive urine- or swab-based diagnostic test is needed.

3. SUMMARY

In some embodiments, methods of detecting the presence or absence of *Trichomonas vaginalis* (TV) in a sample from a subject are provided. In some embodiments, methods of determining whether a subject has a *Trichomonas vaginalis* (TV) infection are provided. In some embodiments, the methods comprise detecting the presence or absence of the TV 40S ribosomal protein (Tv40Srp) gene or RNA in a sample from the subject.

In some embodiments, the subject has not previously been treated for TV infection. In some embodiments, the subject has previously been treated for TV infection. In some embodiments, the previous treatment comprised one or more doses of metronidazole or tinidazole. In some embodiments, the subject does not have any symptoms of TV infection. In some embodiments, the subject has one or more symptoms of TV infection. In some embodiments, the subject has one or more symptoms selected from vaginitis, urethritis, and cervicitis. In some embodiments, the subject is female and has one or more symptoms selected from itching, burning, redness, and/or soreness of the genitals; unusual odor of the genitals; discomfort with urination; and a thin clear, white, yellow, or green discharge. In some embodiments, the subject is pregnant. In some embodiments, the subject is male and has one or more symptoms selected from itching and/or burning inside the penis; burning after ejaculation and/or urination; and penile discharge.

In some embodiments, the method comprises detecting an endogenous control. In some embodiments, the endogenous control is a sample adequacy control. In some embodiments, the endogenous control is a single-copy human gene. In some embodiments, the endogenous control is selected from HMBS, GAPDH, beta actin, and beta globin.

In some embodiments, the method comprises detecting an exogenous control. In some embodiments, the exogenous control is a sample processing control. In some embodiments, the exogenous control comprises a DNA sequence that is not expected to be present in the sample. In some embodiments, the exogenous control is a bacterial gene.

In some embodiments, the method comprises PCR. In some embodiments, the method comprises quantitative PCR. In some embodiments, the PCR reaction takes less than 2 hours, less than 1 hour, or less than 30 minutes from an initial denaturation step through a final extension step.

In some embodiments, the the TV 40S ribosomal protein (Tv40Srp) gene comprises the sequence of SEQ ID NO: 4. In some embodiments, the method comprises contacting nucleic acids from the sample with a first primer pair for detecting the TV 40S ribosomal protein (Tv40Srp) gene or RNA. In some embodiments, the method comprises contacting nucleic acids from the sample with a second primer pair for detecting an endogenous control. In some embodiments, the method comprises contacting nucleic acids from the sample with a third primer pair for detecting an exogenous control.

In some embodiments, the first primer pair comprises a first primer and a second primer, wherein the first primer comprises a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 4, and wherein the second primer comprises a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 4. In some embodiments, the first primer and the second primer each independently comprises 0, 1, or 2 mismatches compared to SEQ ID NO: 4 or its complement. In some embodiments, the first primer pair comprises a first primer consisting of 15 to 30 nucleotides and a second primer consisting of 15 to 30 nucleotides. In some embodiments, the first primer pair comprises a first primer of SEQ ID NO: 1 and a second primer of SEQ ID NO: 2. In some embodiments, the first primer pair produces an amplicon that is 50 to 500 nucleotides long, 50 to 400 nucleotides long, 50 to 300 nucleotides long, 50 to 200 nucleotides long, 50 to 150 nucleotides long, 100 to 300 nucleotides long, 100 to 200 nucleotides long, or 100 to 150 nucleotides long.

In some embodiments, the method comprises forming the Tv40Srp amplicon. In some embodiments, the method comprises contacting the Tv40Srp amplicon with a first probe capable of selectively hybridizing with the Tv40Srp amplicon. In some embodiments, the first probe comprises a detectable label. In some embodiments, the first probe comprises a fluorescent dye and a quencher molecule. In some embodiments, the first probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 4 or SEQ ID NO: 5. In some embodiments, the first probe comprises 0, 1, or 2 mismatches compared to SEQ ID NO: 4 or its complement or compared to SEQ ID NO: 5 or its complement. In some embodiments, the first probe consists of 15 to 30 nucleotides. In some embodiments, the first probe has the sequence of SEQ ID NO: 3.

In some embodiments, the method comprises forming an endogenous control amplicon and/or an exogenous control amplicon. In some embodiments, the method comprises contacting the endogenous control amplicon with a second probe capable of selectively hybridizing with the engoenous control amplicon and/or contacting the exogenous control amplicon with a third probe capable of selectively hybridizing with the exoenous control amplicon. In some embodiments, the second probe and the third probe each comprise a detectable label, wherein the detectable labels may be the same or different. In some embodiments, the detectable labels of the second and third probes are detectably different from the detectable label of the first probe. In some embodiments, the method comprises detecting the Tv40Srp gene or RNA, an endogenous control, and an exogenous control in a single multiplex reaction.

In some embodiments, the sample is selected from a urine sample, an endocervical swab sample, a vaginal swab sample, and a urethral swab sample.

In some embodiments, compositions comprising a first primer pair for detecting a *Trichomonas vaginalis* 40S ribosomal protein (Tv40Srp) gene or RNA are provided. In some embodiments, the composition comprises a second primer pair for detecting an endogenous control. In some embodiments, the endogenous control is a sample adequacy control. In some embodiments, the endogenous control is selected from HMBS, GAPDH, beta actin, and beta globin. In some embodiments, the composition comprises a third primer pair for detecting an exogenous control. In some embodiments, the exogenous control is a sample processing control. In some embodiments, the exogenous control is a bacterial gene.

In some embodiments, the first primer pair comprises a first primer and a second primer, wherein the first primer comprises a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 4, and wherein the second primer comprises a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 4. In some embodiments, the first primer and the second primer each independently comprises 0, 1, or 2 mismatches compared to SEQ ID NO: 4 or its complement. In some embodiments, the first primer pair comprises a first primer consisting of 15 to 30 nucleotides and a second primer consisting of 15 to 30 nucleotides. In some embodiments, the first primer pair comprises a first primer of SEQ ID NO: 1 and a second primer of SEQ ID NO: 2.

In some embodiments, the composition comprises a first probe capable of selectively hybridizing to a Tv40Srp amplicon produced by the first primer pair. In some embodiments, the first probe comprises a detectable label. In some embodiments, the first probe comprises a fluorescent dye and a quencher molecule. In some embodiments, the first probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 4 or SEQ ID NO: 5. In some embodiments, the first probe comprises 0, 1, or 2 mismatches compared to SEQ ID NO: 4 or its complement or compared to SEQ ID NO: 5 or its complement. In some embodiments, the first probe consists of 15 to 30 nucleotides. In some embodiments, the first probe has the sequence of SEQ ID NO: 3. In some embodiments, the Tv40Srp amplicon has the sequence of SEQ ID NO: 5.

In some embodiments, the composition comprises a second probe capable of selectively hybridizing to an endogenous control amplicon produced by the second primer pair. In some embodiments, the endogenous control is a sample adequacy control. In some embodiments, the endogenous control is selected from HMBS, GAPDH, beta actin, and beta globin. In some embodiments, the composition comprises a third probe capable of selectively hybridizing to an exogenous control amplicon produced by the third primer pair. In some embodiments, the exogenous control is a sample processing control. In some embodiments, the exogenous control comprises a DNA sequence that is not expected to be present in the sample. In some embodiments, the exogenous control is a bacterial DNA.

In some embodiments, the composition is a lyophilized composition. In some embodiments, the composition is in solution. In some embodiments, the composition comprises nucleic acids from a sample from a subject being tested for the presence of absence of *Trichomonas vaginalis*.

In some embodiments, kits are provided comprising a first primer pair for detecting a *Trichomonas vaginalis* 40S ribosomal protein (Tv40Srp) gene or RNA. In some embodiments, the kit comprises a second primer pair for detecting an endogenous control, wherein the primer pair for detecting Tv40Srp and the second primer pair are in the same or different compositions in the kit. In some embodiments, the endogenous control is a sample adequacy control. In some embodiments, the endogenous control is selected from HMBS, GAPDH, beta actin, and beta globin. In some embodiments, the kit comprises a third primer pair for detecting an exogenous control, wherein the third primer pair is in the same or different composition from the primer pair for detecting Tv40Srp and the second primer pair. In some embodiments, the exogenous control is a sample processing control. In some embodiments, the exogenous control comprises a DNA sequence that is not expected to be present in the sample. In some embodiments, the exogenous control is a bacterial gene.

In some embodiments, the first primer pair comprises a first primer and a second primer, wherein the first primer comprises a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 4, and wherein the second primer comprises a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 4. In some embodiments, the first primer and the second primer each independently comprises 0, 1, or 2 mismatches compared to SEQ ID NO: 4 or its complement. In some embodiments, the first primer pair comprises a first primer consisting of 15 to 30 nucleotides and a second primer consisting of 15 to 30 nucleotides. In some embodiments, the first primer pair comprises a first primer of SEQ ID NO: 1 and a second primer of SEQ ID NO: 2.

In some embodiments, the kit comprises a first probe capable of selectively hybridizing to a Tv40Srp amplicon produced by the first primer pair, wherein the first probe is in the same or different composition from one or more of the primer pairs. In some embodiments, the first probe comprises a detectable label. In some embodiments, the first probe comprises a fluorescent dye and a quencher molecule. In some embodiments, the first probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 4 or SEQ ID NO: 5. In some embodiments, the first probe comprises 0, 1, or 2 mismatches compared to SEQ ID NO: 4 or its complement or compared to SEQ ID NO: 5 or its complement. In some embodiments, the first probe consists of 15 to 30 nucleotides. In some embodiments, the first probe has the sequence of SEQ ID NO: 3. In some embodiments, the Tv40Srp amplicon has the sequence of SEQ ID NO: 5.

In some embodiments, the kit comprises a second probe capable of selectively hybridizing to an endogenous control amplicon produced by the second primer pair, wherein the second probe is in the same or different composition from one or more of the primer pairs. In some embodiments, the kit comprises a third probe capable of selectively hybridizing to an exogenous control amplicon produced by the third primer pair, wherein the third probe is in the same or different composition from one or more of the primer pairs.

In some embodiments, the kit comprises dNTPs and/or a thermostable polymerase. In some embodiments, the kit comprises one or more lyophilized compositions.

In some embodiments, a primer is provided, wherein the primer consists of the sequence of SEQ ID NO: 1, wherein the primer comprises at least one modified nucleotide. In some embodiments, a primer is provided, wherein the primer consists of the sequence of SEQ ID NO: 2, wherein the primer comprises at least one modified nucleotide. In some embodiments, a probe is provided, wherein the probe consists of the sequence of SEQ ID NO: 3, wherein the probe comprises at least one modified nucleotide and/or a detectable label. In some embodiments, the probe comprises a fluorescent dye and a quencher molecule. In some embodiments, the probe is a fluorescence resonance energy transfer (FRET) probe. In some embodiments, the probe comprises at least one modified nucleotide.

In some embodiments, a composition is provided, wherein the composition comprises a first primer consisting of the sequence of SEQ ID NO: 2 and a second primer consisting of the sequence of SEQ ID NO: 3, wherein the first primer and the second primer each comprises at least one modified nucleotide. In some embodiments, the composition comprises a probe consisting of the sequence of SEQ ID NO: 3, wherein the probe comprises at least one modified nucleotide and/or a detectable label. In some embodiments, the probe comprises a fluorescent dye and a quencher molecule. In some embodiments, the probe is a fluorescence resonance energy transfer (FRET) probe. In some embodiments, the probe comprises at least one modified nucleotide. In some embodiments, the composition is a lyophilized composition. In some embodiments, the composition is in solution. In some embodiments, the composition comprises nucleic acids of a sample from a subject.

Further embodiments and details of the inventions are described below.

4. DETAILED DESCRIPTION

4.1. Definitions

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "detectably different" refers to a set of labels (such as dyes) that can be detected and distinguished simultaneously.

As used herein, the terms "patient" and "subject" are used interchangeably to refer to a human. In some embodiments, the methods described herein may be used on samples from non-human animals.

"*Trichomonas vaginalis*" refers to the protozoan responsible for trichomoniasis, a common sexually transmitted infection that can infect both men and women. Trichomoniasis may be symptomatic or asymptomatic. Symptoms of trichomoniasis include, but are not limited to, vaginitis, urethritis, and cervicitis. Symptoms in females include, but are not limited to, itching, burning, redness, or soreness of the genitals, unusual odor, discomfort with urination, or a thin clear, white, yellow, or green discharge. Symptoms in males include, but are not limited to, itching or burning inside the penis, burning after ejaculation or urination, or penile discharge.

As used herein, the terms "oligonucleotide," "polynucleotide," "nucleic acid molecule," and the like, refer to nucleic acid-containing molecules, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "oligonucleotide," refers to a single-stranded polynucleotide having fewer than 500 nucleotides. In some embodiments, an oligonucleotide is 8 to 200, 8 to 100, 12 to 200, 12 to 100, 12 to 75, or 12 to 50 nucleotides long. Oligonucleotides may be referred to by their length, for example, a 24 residue oligonucleotide may be referred to as a "24-mer."

As used herein, the term "complementary" to a target gene (or target region thereof), and the percentage of "complementarity" of the probe sequence to the target gene sequence is the percentage "identity" to the sequence of target gene or to the reverse complement of the sequence of the target gene. In determining the degree of "complementarity" between probes used in the compositions described herein (or regions thereof) and a target gene, such as those disclosed herein, the degree of "complementarity" is expressed as the percentage identity between the sequence of the probe (or region thereof) and sequence of the target gene or the reverse complement of the sequence of the target gene that best aligns therewith. The percentage is calculated by counting the number of aligned bases that are identical as between the 2 sequences, dividing by the total number of contiguous nucleotides in the probe, and multiplying by 100. When the term "complementary" is used, the subject oligonucleotide is at least 90% complementary to the target molecule, unless indicated otherwise. In some embodiments, the subject oligonucleotide is at least 91%, at least 92%, at least 93%, at least 94%, at least 95%, at least 96%, at least 97%, at least 98%, at least 99%, or 100% complementary to the target molecule.

A "primer" or "probe" as used herein, refers to an oligonucleotide that comprises a region that is complementary to a sequence of at least 8 contiguous nucleotides of a target nucleic acid molecule, such as DNA (e.g., a target gene) or an mRNA (or a DNA reverse-transcribed from an mRNA). In some embodiments, a primer or probe comprises a region that is complementary to a sequence of at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of a target molecule. When a primer or probe comprises a region that is "complementary to at least x contiguous nucleotides of a target molecule," the primer or probe is at least 95% complementary to at least x contiguous nucleotides of the target molecule. In some embodiments, the primer or probe is at least 96%, at least 97%, at least 98%, at least 99%, or 100% complementary to the target molecule.

The term "nucleic acid amplification," encompasses any means by which at least a part of at least one target nucleic acid is reproduced, typically in a template-dependent manner, including without limitation, a broad range of techniques for amplifying nucleic acid sequences, either linearly or exponentially. Exemplary means for performing an amplifying step include polymerase chain reaction (PCR), ligase chain reaction (LCR), ligase detection reaction (LDR), multiplex ligation-dependent probe amplification (MLPA), ligation followed by Q-replicase amplification, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), digital amplification, and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18- (2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

Unless otherwise indicated, the term "hybridize" is used herein refer to "specific hybridization" which is the binding, duplexing, or hybridizing of a nucleic acid molecule preferentially to a particular nucleotide sequence, in some embodiments, under stringent conditions. The term "stringent conditions" refers to conditions under which a probe will hybridize preferentially to its target sequence, and to a lesser extent to, or not at all to, other sequences. A "stringent hybridization" and "stringent hybridization wash conditions" in the context of nucleic acid hybridization (e.g., as in array, Southern, or Northern hybridization) are sequence-dependent and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. ("Tijssen"). Generally, highly stringent hybridization and wash conditions for filter hybridizations are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. Dependency of hybridization stringency on buffer composition, temperature, and probe length are well known to those of skill in the art (see, e.g., Sambrook and Russell (2001) Molecular Cloning: A Laboratory Manual (3rd ed.) Vol. 1-3, Cold Spring Harbor Laboratory, Cold Spring Harbor Press, N.Y.).

A "sample," as used herein, includes urine samples (including samples derived from urine samples), endocervical swabs, and patient-collected vaginal swabs, and other types of human samples. In some embodiments, a urine sample is a "first catch" urine sample, which is a sample taken as a subject first begins to urinate. As used herein, urine samples include, but are not limited to, whole urine, a sample comprising cells from a urine sample, a sample comprising the cell pellet isolated by centrifugation of a urine sample, a sample comprising cells isolated by filtration of a urine sample, and the like. In some embodiments, a urine sample comprises a buffer, such as a preservative. In some embodiments, a sample is a human sample other than a urine sample, such as an endocervical swab or a vaginal swab, including a patient-collected vaginal swab, and a urethral swab. In some embodiments, a swab sample comprises a buffer, such as a preservative.

An "endogenous control," as used herein refers to a moiety that is naturally present in the sample to be used for detection. In some embodiments, an endogenous control is a "sample adequacy control" (SAC), which may be used to determine whether there was sufficient sample used in the assay, or whether the sample comprised sufficient biological material, such as cells. In some embodiments, an SAC is a single copy human gene. In some embodiments, an endogenous control, such as an SAC, is selected that can be detected in the same manner as the target gene is detected and, in some embodiments, simultaneously with the target gene.

An "exogenous control," as used herein, refers to a moiety that is added to a sample or to an assay, such as a "sample processing control" (SPC). In some embodiments, an exogenous control is included with the assay reagents. An exogenous control is typically selected that is not expected to be present in the sample to be used for detection, or is present at very low levels in the sample such that the amount of the moiety naturally present in the sample is either undetectable or is detectable at a much lower level than the amount added to the sample as an exogenous control. In some embodiments, an exogenous control comprises a nucleotide sequence that is not expected to be present in the sample type used for detection of the target gene. In some embodiments, an exogenous control comprises a nucleotide sequence that is not known to be present in the species from whom the sample is taken. In some embodiments, an exogenous control comprises a nucleotide sequence from a different species than the subject from whom the sample was taken. In some embodiments, an exogenous control comprises a nucleotide sequence that is not known to be present in any species. In some embodiments, an exogenous control is selected that can be detected in the same manner as the target gene is detected and, in some embodiments, simultaneously with the target gene. In some embodiments, an exogenous control is a bacterial DNA. In some embodiments, the bacterium is a species not expected to be found in the sample type being tested.

In the sequences herein, "U" and "T" are used interchangeably, such that both letters indicate a uracil or thymine at that position. One skilled in the art will understand from the context and/or intended use whether a uracil or thymine is intended and/or should be used at that position in the sequence. For example, one skilled in the art would understand that native RNA molecules typically include uracil, while native DNA molecules typically include thymine. Thus, where an RNA sequence includes "T", one skilled in the art would understand that that position in the native RNA is likely a uracil.

In the present disclosure, "a sequence selected from" encompasses both "one sequence selected from" and "one or more sequences selected from." Thus, when "a sequence selected from" is used, it is to be understood that one, or more than one, of the listed sequences may be chosen.

4.2. Detecting *Trichomonas vaginalis*

The present inventors have developed an assay for detecting *Trichomonas vaginalis* (TV). In some embodiments, the assay comprises detecting the TV 40S ribosomal protein (Tv40Srp) gene. In some embodiments, the assay comprises detecting RNA transcribed from the TV 40S ribosomal protein (Tv40Srp) gene. The present assay relies on the polymerase chain reaction (PCR), and can be carried out in a substantially automated manner using a commercially available nucleic acid amplification system. Exemplary non-limiting nucleic acid amplification systems that can be used to carry out the methods of the invention include the GeneXpert® system, a GeneXpert® Infinity system, and a Smartcycler System (Cepheid, Sunnyvale, Calif.). The present assay can be completed in under 3 hours, and in some embodiments, under 2 hours, using an automated system, for example, the GeneXpert® system.

4.2.1. General Methods

Compositions and methods for detecting *Trichomonas vaginalis* (TV) are provided. In some embodiments, the method comprises detecting the TV 40S ribosomal protein (Tv40Srp) gene.

In some embodiments, a method of detecting *Trichomonas vaginalis* (TV) in a subject comprises detecting the presence of the TV 40S ribosomal protein (Tv40Srp) gene in a sample from the subject. In some embodiments, the sample is selected from a urine sample, an endocervical swab, and a vaginal swab. In some embodiments, the urine sample is a first catch urine sample.

In some embodiments, a method of detecting TV further comprises detecting at least one endogenous control, such as a sample adequacy control (SAC). In some embodiments, a method of detecting TV further comprises detecting at least one exogenous control, such as a sample processing control (SPC). In some embodiments, a method of detecting TV further comprises detecting at least one endogenous control and at least one exogenous control.

In some embodiments, a method of detecting TV comprises detecting the TV 40S ribosomal protein (Tv40Srp) gene in a sample. In some embodiments, a method of detecting TV further comprises detecting a sample adequacy control (SAC), such as a single copy human gene. In some embodiments, a method of detecting TV further comprises detecting a sample processing control (SPC), such as an exogenously added bacterial DNA. In some embodiments, a method of detecting TV further comprises detecting an SAC and an SPC.

In the present disclosure, the term "target gene" is used for convenience to refer to the TV 40S ribosomal protein (Tv40Srp) gene, and also to exogenous and/or endogenous controls. Thus, it is to be understood that when a discussion is presented in terms of a target gene, that discussion is specifically intended to encompass the TV 40S ribosomal protein (Tv40Srp) gene, the endogenous control(s) (e.g., SAC), and the exogenous control(s) (e.g., SPC).

In some embodiments, the presence of the TV 40S ribosomal protein (Tv40Srp) gene is detected in a urine sample. In some embodiments, the target gene is detected in a urine sample to which a buffer (such as a preservative) has been added. In some embodiments, the buffer is added to a urine sample at a ratio of 1:1, 1:2, 1:3, 1:4, 1:5, 1:6, 1:7, 1:8, 1:9, or 1:10 buffer:urine. In some embodiments, the presence of the TV 40S ribosomal protein (Tv40Srp) gene is detected in an endocervical swab sample or a vaginal swab sample. In some embodiments, the vaginal swab is a patient-collected vaginal swab. In some embodiments, the target gene is detected in an endocervical swab sample or a vaginal swab sample that has been placed in a buffer (such as a preservative). In some embodiments, a swab is placed in 1 mL, 2 mL, 2.5 mL of buffer.

In some embodiments, detection of the TV 40S ribosomal protein (Tv40Srp) gene in a sample from a subject indicates the presence of *Trichomonas vaginalis* in the subject. In some embodiments, the detecting is done quantitatively. In other embodiments, the detecting is done qualitatively. In some embodiments, detecting a target gene comprises forming a complex comprising a polynucleotide and a nucleic acid selected from a target gene, a DNA amplicon of a target gene, and a complement of a target gene. In some embodiments, detecting a target gene comprises PCR. In some embodiments, detecting a target gene comprises quantitative PCR or real-time PCR. In some embodiments, a sample adequacy control (SAC) and/or a sample processing control (SPC) is detected in the same assay as the target gene. In some embodiments, if the TV 40S ribosomal protein (Tv40Srp) gene is detected, TV is considered to be detected even if the SPC and/or SAC are not detected in the assay. In some embodiments, if the TV 40S ribosomal protein (Tv40Srp) gene is not detected, TV is considered to be not detected only if the SPC and SAC are also detected in the assay.

In some embodiments, the presence of the TV 40S ribosomal protein (Tv40Srp) gene can be measured in samples collected at one or more times from a subject to monitor treatment for TV infection in the subject. Treatments include, but are not limited to, a single dose or multiple doses of metronidazole or tinidazole. In some embodiments, a subject with a history of TV infection is monitored for recurrence of TV by detecting the presence or absence of the TV 40S ribosomal protein (Tv40Srp) gene at regular or semi-regular intervals. In some such embodiments, the patient is monitored by detecting the presence or absence of the TV 40S ribosomal protein (Tv40Srp) gene at least once per month, at least once every two months, at least once every three months, at least once every four months, at least once every five months, at least once every six months, at least once every nine months, at least once per year, or at least once every two years.

In some embodiments, the present assay may be used as part of routine and/or preventative healthcare for a subject. That is, in some embodiments, the present assay may be used to test an individual for TV infection whether or not the individual has exhibited symptoms of TV infection or has a history of TV infection. In some embodiments, the present assay is used to detect TV infection in subjects who are pregnant and/or who are attempting to become pregnant. In some instances, pregnant women with TV are more likely to experience pre-term delivery and/or have babies with low birth weight (less than 5.5 pounds).

In some embodiments, a sample to be tested is a urine sample (such as a first catch urine sample), or is derived from a urine sample. In some embodiments, a buffer (such as a preservative) is added to the urine sample. In some embodiments, the buffer is added to the urine sample within 1 hour, within 2 hours, within 3 hours, within 4 hours, within 5 hours, within 6 hours, within 7 hours, or within 8 hours of sample collection.

In some embodiments, a sample to be tested is an endocervical swab sample or a vaginal swab sample. In some embodiments, the swab is placed in a buffer. In some embodiments, the swab is immediately placed in the buffer. In some embodiments, the swab is placed in the buffer within 1 hour, within 2 hours, within 3 hours, within 4 hours, within 5 hours, within 6 hours, within 7 hours, or within 8 hours of sample collection.

In some embodiments, less than 5 ml, less than 4 ml, less than 3 ml, less than 2 ml, less than 1 ml, or less than 0.75 ml of urine are used in the present methods. In some embodiments, 0.1 ml to 1 ml of urine is used in the present methods.

In some embodiments, the sample to be tested is another bodily fluid, such as blood, sputum, mucus, saliva, vaginal or penile discharge, semen, etc.

The clinical sample to be tested is, in some embodiments, fresh (i.e., never frozen). In other embodiments, the sample is a frozen specimen. In some embodiments, the sample is a tissue sample, such as a formalin-fixed paraffin embedded sample. In some embodiments, the sample is a liquid cytology sample.

In some embodiments, the sample to be tested is obtained from an individual who has one or more symptoms of TV infection. Nonlimiting exemplary symptoms of TV infection include vaginitis, urethritis, and cervicitis; in females: itching, burning, redness, or soreness of the genitals, unusual odor, discomfort with urination, and a thin clear, white, yellow, or green discharge; and in males: itching or burning inside the penis, burning after ejaculation or urination, and penile discharge. In some embodiments, the sample to be tested is obtained from an individual who has previously been diagnosed with TV infection. In some such embodiments, the individual is monitored for recurrence of TV infection.

In some embodiments, methods described herein can be used for routine screening of healthy individuals with no risk factors. In some embodiments, methods described herein are used to screen asymptomatic individuals, for example, during routine or preventative care. In some embodiments, methods described herein are used to screen women who are pregnant or who are attempting to become pregnant.

In some embodiments, the methods described herein can be used to assess the effectiveness of a treatment for TV infection in a patient.

In some embodiments, use of the the TV 40S ribosomal protein (Tv40Srp) gene for detecting TV infection is provided. In some embodiments, use of the the TV 40S ribosomal protein (Tv40Srp) gene for monitoring recurrence of TV infection is provided.

In any of the embodiments described herein, the TV 40S ribosomal protein (Tv40Srp) gene may be detected in the same assay reaction as a sample processing control (SPC) and/or sample adequacy control (SAC).

In some embodiments, a method of facilitating detection of TV infection in a subject is provided. Such methods comprise detecting the presence or absence of the TV 40S ribosomal protein (Tv40Srp) gene in a sample from the subject. In some embodiments, information concerning the presence or absence of the TV 40S ribosomal protein (Tv40Srp) gene in the sample from the subject is communicated to a medical practitioner. A "medical practitioner," as used herein, refers to an individual or entity that diagnoses and/or treats patients, such as a hospital, a clinic, a physician's office, a physician, a nurse, or an agent of any of the aforementioned entities and individuals. In some embodiments, detecting the presence or absence of TV 40S ribosomal protein (Tv40Srp) gene is carried out at a laboratory that has received the subject's sample from the medical practitioner or agent of the medical practitioner. The laboratory carries out the detection by any method, including those described herein, and then communicates the results to the medical practitioner. A result is "communicated," as used herein, when it is provided by any means to the medical practitioner. In some embodiments, such communication may be oral or written, may be by telephone, in person, by e-mail, by mail or other courier, or may be made by directly depositing the information into, e.g., a database accessible by the medical practitioner, including databases not controlled by the medical practitioner. In some embodiments, the information is maintained in electronic form. In some embodiments, the information can be stored in a memory or other computer readable medium, such as RAM, ROM, EEPROM, flash memory, computer chips, digital video discs (DVD), compact discs (CDs), hard disk drives (HDD), magnetic tape, etc.

In some embodiments, methods of detecting TV are provided. In some embodiments, methods of diagnosing TV infection are provided. In some embodiments, the method comprises obtaining a sample from a subject and providing the sample to a laboratory for detection of the TV 40S ribosomal protein (Tv40Srp) gene in the sample. In some embodiments, the method further comprises receiving a communication from the laboratory that indicates the presence or absence of the TV 40S ribosomal protein (Tv40Srp) gene in the sample. A "laboratory," as used herein, is any facility that detects the target gene in a sample by any method, including the methods described herein, and communicates the result to a medical practitioner. In some embodiments, a laboratory is under the control of a medical practitioner. In some embodiments, a laboratory is not under the control of the medical practitioner.

When a laboratory communicates the result of detecting the presence or absence of the TV 40S ribosomal protein (Tv40Srp) gene to a medical practitioner, in some embodiments, the laboratory indicates whether or not the TV 40S ribosomal protein (Tv40Srp) gene was detected in the sample. In some embodiments, the laboratory indicates whether the sample comprises *Trichomonas vaginalis* (TV), by indicating, for example, "TV positive" or "TV negative" or "TV present" or "TV absent," and the like.

As used herein, when a method relates to detecting TV, determining the presence of TV, monitoring for TV, and/or diagnosing TV infection, the method includes activities in which the steps of the method are carried out, but the result is negative for the presence of TV. That is, detecting, determining, monitoring, and diagnosing TV or TV infection include instances of carrying out the methods that result in either positive or negative results.

In some embodiments, at least one endogenous control (e.g., an SAC) and/or at least one exogenous control (e.g., an SPC) are detected simultaneously with the TV 40S ribosomal protein (Tv40Srp) gene in a single reaction.

4.2.2. Exemplary Controls

In some embodiments, an assay described herein comprises detecting the TV 40S ribosomal protein (Tv40Srp) gene and at least one endogenous control. In some embodiments, the endogenous control is a sample adequacy control (SAC). In some such embodiments, if the TV 40S ribosomal protein (Tv40Srp) gene is not detected in a sample, and the SAC is also not detected in the sample, the assay result is considered "invalid" because the sample may have been insufficient. While not intending to be bound by any particular theory, an insufficient sample may be too dilute, contain too little cellular material, contain an assay inhibitor, etc. In some embodiments, the failure to detect an SAC may indicate that the assay reaction failed. In some embodiments, an endogenous control (such as an SAC) is a single-copy human gene. Nonlimiting exemplary SACs include human hydroxymethyl-bilane synthase (HMBS), glyceraldehyde-3-phosphate dehydrogenase (GAPDH), beta actin, beta2-microglobin, cyclooxygenase 1, hypoxanthine phosphoribosyl-transferase, porphobilinogen deaminase, and the transferrin receptor.

In some embodiments, an assay described herein comprises detecting the TV 40S ribosomal protein (Tv40Srp) gene and at least one exogenous control. In some embodiments, the exogenous control is a sample processing control (SPC). In some such embodiments, if the TV 40S ribosomal protein (Tv40Srp) gene is not detected in a sample, and the SPC is also not detected in the sample, the assay result is considered "invalid" because there may have been an error in sample processing, including but not limited to, failure of the assay. Nonlimiting exemplary errors in sample processing include, inadequate sample processing, the presence of an assay inhibitor, compromised reagents, etc. In some embodiments, an exogenous control (such as an SPC) is added to a sample. In some embodiments, an exogenous control (such as an SPC) is added during performance of an assay, such as with one or more buffers or reagents. In some embodiments, when a GeneXpert® system is to be used, the SPC is included in the GeneXpert® cartridge. In some embodiments, an exogenous control (such as an SPC) is a DNA sequence that is not expected to be present in the sample being assayed. Nonlimiting exemplary SPCs include bacterial genes not expected to be present in the sample being assayed.

In some embodiments, an endogenous control and/or an exogenous control is detected contemporaneously, such as in the same assay, as detection of the TV 40S ribosomal protein (Tv40Srp) gene in a sample. In some embodiments, an assay comprises reagents for detecting the TV 40S ribosomal protein (Tv40Srp) gene, an exogenous control, and an endogenous control simultaneously in the same assay reaction. In some such embodiments, for example, an assay reaction comprises a primer set for amplifying the TV 40S ribosomal protein (Tv40Srp) gene, a primer set for amplifying an endogenous control, and a primer set for amplifying an exogenous control, and labeled probes for detecting the amplification products (such as, for example, TaqMan® probes).

4.2.3. Exemplary Sample Preparation 4.2.3.1. Exemplary Buffers

In some embodiments, a buffer is added to a urine sample. In some embodiments, the buffer is added within one hour, two hours, three hours, or six hours of the time the urine sample was collected (e.g., voided). In some embodiments, a buffer is added to the urine sample within one hour, two hours, three hours, or six hours before the sample is analyzed by the methods described herein.

In some embodiments, a swab sample is placed in a buffer. In some embodiments, the swab sample is placed in the buffer within one hour, two hours, three hours, or six hours of the time the swab sample was collected. In some embodiments, the swab sample is placed in a buffer within one hour, two hours, three hours, or six hours before the sample is analyzed by the methods described herein.

Non-limiting exemplary commercial buffers include PreservCyt (Hologic, Bedford, Mass.), SurePath (BD, Franklin Lakes, N.J.), and CyMol (Copan Diagnostics, Murrietta, Calif.).

4.2.3.2. Exemplary DNA Preparation

Sample DNA can be prepared by any appropriate method. In some embodiments, target DNA is prepared by contacting a sample with a lysis buffer and binding DNA to a DNA binding substrate, such as a glass or silica substrate. The binding substrate may have any suitable form, such as a particulate, porous solid, or membrane form. For example, the support may comprise hydroxycellulose, glass fiber, cellulose, nitrocellulose, zirconium hydroxide, titanium (IV) oxide, silicon dioxide, zirconium silicate, or silica particles (e.g., see U.S. Pat. No. 5,234,809). Many such DNA binding substrates are known in the art.

In some embodiments, DNA is detected in a lysate without first isolating or separating the DNA. In some some embodiments, the sample is subject to a lysis step to release the DNA. Non-limiting exemplary lysis methods include sonication (for example, for 2-15 seconds, 8-18 µm at 36 kHz); chemical lysis, for example, using a detergent; and various commercially available lysis reagents. In some embodiments, DNA is detected are measured in a sample in which DNA has been isolated or separated from at least some other cellular components.

When the methods discussed herein indicate that a target gene is detected, such detection may be carried out on a complement of a target gene instead of, or in addition to, the target gene sequence shown herein. In some embodiments, when the complement of a target gene is detected, a polynucleotide for detection is used that is complementary to the complement of the target gene. In some some embodiments, a polynucleotide for detection comprises at least a portion that is at least 90%, at least 95%, or 100% identical in sequence to the target gene, although it may comprise modified nucleotides.

4.2.4. Exemplary Analytical Methods

As described above, methods are presented for detecting *Trichomonas vaginalis*. The methods comprise detecting the presence of the TV 40S ribosomal protein (Tv40Srp) gene in a sample from a subject. In some embodiments, the method further comprises detecting at least one endogenous control (such as an SAC) and/or at least one exogenous control (such as an SPC). In some embodiments, detection of the TV 40S ribosomal protein (Tv40Srp) gene indicates the presence of TV, even if the endogenous control and/or exogenous control is not detected in the assay. In some embodiments, if the TV 40S ribosomal protein (Tv40Srp) gene is not detected, the result is considered to be negative for TV only if the controls are detected. In some embodiments, if the TV 40S ribosomal protein (Tv40Srp) gene is not detected, the result is considered to be negative for TV only if the endogenous control and exogenous control are detected.

Any analytical procedure capable of permitting specific detection of a target gene may be used in the methods herein presented. Exemplary nonlimiting analytical procedures include, but are not limited to, nucleic acid amplification methods, PCR methods, isothermal amplification methods, and other analytical detection methods known to those skilled in the art.

In some embodiments, the method of detecting a target gene, such as the TV 40S ribosomal protein (Tv40Srp) gene, comprises amplifying the gene and/or a complement thereof. Such amplification can be accomplished by any method. Exemplary methods include, but are not limited to, isothermal amplification, real time PCR, endpoint PCR, and amplification using T7 polymerase from a T7 promoter annealed to a DNA, such as provided by the SenseAmp Plus™ Kit available at Implen, Germany.

When a target gene is amplified, in some embodiments, an amplicon of the target gene is formed. An amplicon may be single stranded or double-stranded. In some embodiments, when an amplicon is single-stranded, the sequence of the amplicon is related to the target gene in either the sense or antisense orientation. In some embodiments, an amplicon of a target gene is detected rather than the target gene itself. Thus, when the methods discussed herein indicate that a target gene is detected, such detection may be carried out on an amplicon of the target gene instead of, or in addition to, the target gene itself. In some embodiments, when the amplicon of the target gene is detected rather than the target gene, a polynucleotide for detection is used that is complementary to the complement of the target gene. In some embodiments, when the amplicon of the target gene is detected rather than the target gene, a polynucleotide for detection is used that is complementary to the target gene. Further, in some embodiments, multiple polynucleotides for detection may be used, and some polynucleotides may be complementary to the target gene and some polynucleotides may be complementary to the complement of the target gene.

In some embodiments, the method of detecting the TV 40S ribosomal protein (Tv40Srp) gene comprises PCR, as described below. In some embodiments, detecting one or more target genes comprises real-time monitoring of a PCR reaction, which can be accomplished by any method. Such methods include, but are not limited to, the use of TaqMan®, molecular beacons, or Scorpion probes (i.e., energy transfer (ET) probes, such as FRET probes) and the use of intercalating dyes, such as SYBR green, EvaGreen, thiazole orange, YO-PRO, TO-PRO, etc.

Nonlimiting exemplary conditions for amplifying a target gene are as follows. An exemplary cycle comprises an initial denaturation at 90° C. to 100° C. for 30 seconds to 5 minutes, followed by cycling that comprises denaturation at 90° C. to 100° C. for 1 to 10 seconds, followed by annealing and amplification at 60° C. to 75° C. for 10 to 30 seconds. A further exemplary cycle comprises 1 minute at 95° C., followed by up to 40 cycles of 5 seconds at 92.5° C., 20 seconds at 68° C. In some embodiments, for the first cycle following the initial denaturation step, the cycle denaturation step is omitted. In some embodiments, Taq polymerase is used for amplification. In some embodiments, the cycle is carried out at least 10 times, at least 15 times, at least 20 times, at least 25 times, at least 30 times, at least 35 times, at least 40 times, or at least 45 times. In some embodiments, Taq is used with a hot start function. In some embodiments, the amplification reaction occurs in a GeneXpert® cartridge, and amplification of the TV 40S ribosomal protein (Tv40Srp) gene, an endogenous control, and an exogenous control occurs in the same reaction. In some embodiments, detection of the TV 40S ribosomal protein (Tv40Srp) gene occurs in less than 3 hours, less than 2.5 hours, less than 2 hours, less than 1 hour, or less than 30 minutes from initial denaturation through the last extension.

In some embodiments, detection of a target gene comprises forming a complex comprising a polynucleotide that is complementary to a target gene or to a complement thereof, and a nucleic acid selected from the target gene, a DNA amplicon of the target gene, and a complement of the target gene. Thus, in some embodiments, the polynucleotide forms a complex with a target gene. In some embodiments, the polynucleotide forms a complex with a complement of the target gene. In some embodiments, the polynucleotide forms a complex with a DNA amplicon of the target gene. When a double-stranded DNA amplicon is part of a complex, as used herein, the complex may comprise one or both strands of the DNA amplicon. Thus, in some embodiments, a complex comprises only one strand of the DNA amplicon. In some embodiments, a complex is a triplex and comprises the polynucleotide and both strands of the DNA amplicon. In some embodiments, the complex is formed by hybridization between the polynucleotide and the target gene, complement of the target gene, or DNA amplicon of the target gene. The polynucleotide, in some embodiments, is a primer or probe.

In some embodiments, a method comprises detecting the complex. In some embodiments, the complex does not have to be associated at the time of detection. That is, in some embodiments, a complex is formed, the complex is then dissociated or destroyed in some manner, and components from the complex are detected. An example of such a system is a TaqMan® assay. In some embodiments, when the polynucleotide is a primer, detection of the complex may comprise amplification of the target gene, a complement of the target gene, or a DNA amplicon of the target gene.

In some embodiments the analytical method used for detecting at least one target gene in the methods set forth herein includes real-time quantitative PCR. In some embodiments, the analytical method used for detecting at least one target gene includes the use of a TaqMan® probe. The assay uses energy transfer ("ET"), such as fluorescence resonance energy transfer ("FRET"), to detect and quantitate the synthesized PCR product. Typically, the TaqMan® probe comprises a fluorescent dye molecule coupled to the 5'-end and a quencher molecule coupled to the 3'-end, such that the dye and the quencher are in close proximity, allowing the quencher to suppress the fluorescence signal of the dye via FRET. When the polymerase replicates the chimeric amplicon template to which the TaqMan® probe is bound, the 5'-nuclease of the polymerase cleaves the probe, decoupling the dye and the quencher so that the dye signal (such as fluorescence) is detected. Signal (such as fluorescence) increases with each PCR cycle proportionally to the amount of probe that is cleaved.

In some embodiments, a target gene is considered to be detected if any signal is generated from the TaqMan probe during the PCR cycling. For example, in some embodiments, if the PCR includes 40 cycles, if a signal is generated at any cycle during the amplification, the target gene is considered to be present and detected. In some some embodiments, if no signal is generated by the end of the PCR cycling, the target gene is considered to be absent and not detected.

In some embodiments, quantitation of the results of real-time PCR assays is done by constructing a standard curve from a nucleic acid of known concentration and then extrapolating quantitative information for target genes of unknown concentration. In some embodiments, the nucleic acid used for generating a standard curve is a DNA (for example, an endogenous control, or an exogenous control). In some embodiments, the nucleic acid used for generating a standard curve is a purified double-stranded plasmid DNA or a single-stranded DNA generated in vitro.

In some embodiments, in order for an assay to indicate that TV is not present in a sample, the Ct values for an endogenous control (such as an SAC) and/or an exogenous control (such as an SPC) must be within a previously-determined valid range. That is, in some embodiments, the absence of TV cannot be confirmed unless the controls are detected, indicating that the assay was successful. Ct values are inversely proportional to the amount of nucleic acid target in a sample.

In some embodiments, a threshold Ct (or a "cutoff Ct") value for a target gene (including an endogenous control and/or exogenous control), below which the gene is considered to be detected, has previously been determined. In some embodiments, a threshold Ct is determined using substantially the same assay conditions and system (such as a GeneXpert®) on which the samples will be tested.

In addition to the TagMan® assays, other real-time PCR chemistries useful for detecting and quantitating PCR products in the methods presented herein include, but are not limited to, Molecular Beacons, Scorpion probes and intercalating dyes, such as SYBR Green, EvaGreen, thiazole orange, YO-PRO, TO-PRO, etc., which are discussed below.

In various embodiments, real-time PCR detection is utilized to detect, in a single multiplex reaction, the TV 40S ribosomal protein (Tv40Srp) gene, an endogenous control, and an exogenous control. In some multiplex embodiments, a plurality of probes, such as TaqMan® probes, each specific for a different target, is used. In some embodiments, each target gene-specific probe is spectrally distinguishable from the other probes used in the same multiplex reaction.

Real-time PCR is performed using any PCR instrumentation available in the art. Typically, instrumentation used in real-time PCR data collection and analysis comprises a thermal cycler, optics for fluorescence excitation and emission collection, and optionally a computer and data acquisition and analysis software.

In some embodiments, detection and/or quantitation of real-time PCR products is accomplished using a dye that binds to double-stranded DNA products, such as SYBR Green, EvaGreen, thiazole orange, YO-PRO, TO-PRO, etc. In some embodiments, the analytical method used in the methods described herein is a DASL® (DNA-mediated Annealing, Selection, Extension, and Ligation) Assay. In some embodiments, the analytical method used for detecting and quantifying the target genes in the methods described herein is a bead-based flow cytometric assay. See Lu J. et al. (2005) *Nature* 435:834-838, which is incorporated herein by reference in its entirety. An example of a bead-based flow cytometric assay is the xMAP® technology of Luminex, Inc. See www.luminexcorp.com/technology/index.html. In some embodiments, the analytical method used for detecting and quantifying the levels of the at least one target gene in the methods described herein is by gel electrophoresis and detection with labeled probes (e.g., probes labeled with a radioactive or chemiluminescent label), such as by northern blotting. In some embodiments, exemplary probes contain one or more affinity-enhancing nucleotide analogs as discussed below, such as locked nucleic acid ("LNA") analogs, which contain a bicyclic sugar moiety instead of deoxyribose or ribose sugars. See, e.g., Varallyay, E. et al. (2008) Nature Protocols 3(2):190-196, which is incorporated herein by reference in its entirety. In some embodiments, detection and quantification of one or more target genes is accomplished using microfluidic devices and single-molecule detection.

Optionally, the sample DNA is modified before hybridization. The target DNA/probe duplex is then passed through channels in a microfluidic device and that comprise detectors that record the unique signal of the 3 labels. In this way, individual molecules are detected by their unique signal and counted. See U.S. Pat. Nos. 7,402,422 and 7,351,538 to Fuchs et al., U.S. Genomics, Inc., each of which is incorporated herein by reference in its entirety.

4.2.5. Exemplary Automation and Systems

In some embodiments, gene expression is detected using an automated sample handling and/or analysis platform. In some embodiments, commercially available automated analysis platforms are utilized. For example, in some embodiments, the GeneXpert® system (Cepheid, Sunnyvale, Calif.) is utilized.

The present invention is illustrated for use with the GeneXpert system. Exemplary sample preparation and analysis methods are described below. However, the present invention is not limited to a particular detection method or analysis platform. One of skill in the art recognizes that any number of platforms and methods may be utilized.

The GeneXpert® utilizes a self-contained, single use cartridge. Sample extraction, amplification, and detection may all carried out within this self-contained "laboratory in a cartridge." (See e.g., U.S. Pat. Nos. 5,958,349, 6,403,037, 6,440,725, 6,783,736, 6,818,185; each of which is herein incorporated by reference in its entirety.)

Components of the cartridge include, but are not limited to, processing chambers containing reagents, filters, and capture technologies useful to extract, purify, and amplify target nucleic acids. A valve enables fluid transfer from chamber to chamber and contain nucleic acids lysis and filtration components. An optical window enables real-time optical detection. A reaction tube enables very rapid thermal cycling.

In some embodiments, the GenXpert® system includes a plurality of modules for scalability. Each module includes a plurality of cartridges, along with sample handling and analysis components.

After the sample is added to the cartridge, the sample is contacted with lysis buffer and released DNA is bound to a DNA-binding substrate such as a silica or glass substrate. The sample supernatant is then removed and the DNA eluted in an elution buffer such as a Tris/EDTA buffer. The eluate may then be processed in the cartridge to detect target genes as described herein. In some embodiments, the eluate is used to reconstitute at least some of the PCR reagents, which are present in the cartridge as lyophilized particles.

In some embodiments, PCR is used to amplify and analyze the presence of the target genes. In some embodiments, the PCR uses Taq polymerase with hot start function, such as AptaTaq (Roche). In some embodiments, the initial denaturation is at 90° C. to 100° C. for 30 seconds to 5 minutes; the cycling denaturation temperature is 90° C. to 100° C. for 1 to 10 seconds; the cycling anneal and amplification temperature is 60° C. to 75° C. for 10 to 30 seconds; and up to 50 cycles are performed.

In some embodiments, a double-denature method is used to amplify low copy number targets. A double-denature method comprises, in some embodiments, a first denaturation step followed by addition of primers and/or probes for detecting target genes. All or a substantial portion of the DNA-containing sample (such as a DNA eluate) is then denatured a second time before, in some instances, a portion of the sample is aliquotted for cycling and detection of the target genes. While not intending to be bound by any particular theory, the double-denature protocol may increase the chances that a low copy number target gene (or its complement) will be present in the aliquot selected for cycling and detection because the second denaturation effectively doubles the number of targets (i.e., it separates the target and its complement into two separate templates) before an aliquot is selected for cycling. In some embodiments, the first denaturation step comprises heating to a temperature of 90° C. to 100° C. for a total time of 30 seconds to 5 minutes. In some embodiments, the second denaturation step comprises heating to a temperature of 90° C. to 100° C. for a total time of 5 seconds to 3 minutes. In some embodiments, the first denaturation step and/or the second denaturation step is carried out by heating aliquots of the sample separately. In some embodiments, each aliquot may be heated for the times listed above. As a non-limiting example, a first denaturation step for a DNA-containing sample (such as a DNA eluate) may comprise heating at least one, at least two, at least three, or at least four aliquots of the sample separately (either sequentially or simultaneously) to a temperature of 90° C. to 100° C. for 60 seconds each. As a non-limiting example, a second denaturation step for a DNA-containing sample (such as a DNA eluate) containing enzyme, primers, and probes may comprise heating at least one, at least two, at least three, or at least four aliquots of the eluate separately (either sequentially or simultaneously) to a temperature of 90° C. to 100° C. for 5 seconds each. In some embodiments, an aliquot is the entire DNA-containing sample (such as a DNA eluate). In some embodiments, an aliquot is less than the entire DNA-containing sample (such as a DNA eluate).

In some embodiments, target genes in a DNA-containing sample, such as a DNA eluate, are detected using the following protocol: One or more aliquots of the DNA-containing sample are heated separately to 95° C. for 60 seconds each. The enzyme and primers and probes are added to the DNA-containing sample and one or more aliquots are heated separately to 95° C. for 5 seconds each. At least one aliquot of the DNA-containing sample containing enzyme, primers, and probes is then heated to 94° C. for 60 seconds. The aliquot is then cycled 45 times with the following 2-step cycle: (1) 94° C. for 5 seconds, (2) 66° C. for 30 seconds.

The present invention is not limited to particular primer and/or probe sequences. Exemplary amplification primers and detection probes are described in the Examples.

In some embodiments, an off-line centrifugation is used, for example, with samples with low cellular content. The sample, with or without a buffer added, is centrifuged and the supernatant removed. The pellet is then resuspended in a smaller volume of either supernatant or the buffer. The resuspended pellet is then analyzed as described herein.

4.2.6. Exemplary Data Analysis

In some embodiments, the presence of TV is detected if the Ct value for the TV 40S ribosomal protein (Tv40Srp) gene is below a certain threshold. In some embodiments the valid range of Ct values is 9 to 39.9 Ct. In some such embodiments, if no amplification above background is observed from the TV-specific primers after 40 cycles, the sample is considered to be negative for TV.

In some embodiments, a computer-based analysis program is used to translate the raw data generated by the detection assay into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence of TV) for the subject, with or without recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

4.2.7. Exemplary Polynucleotides

In some embodiments, polynucleotides are provided. In some embodiments, synthetic polynucleotides are provided. Synthetic polynucleotides, as used herein, refer to polynucleotides that have been synthesized in vitro either chemically or enzymatically. Chemical synthesis of polynucleotides includes, but is not limited to, synthesis using polynucleotide synthesizers, such as OligoPilot (GE Healthcare), ABI 3900 DNA Synthesizer (Applied Biosystems), and the like. Enzymatic synthesis includes, but is not limited to, producing polynucleotides by enzymatic amplification, e.g., PCR. A polynucleotide may comprise one or more nucleotide analogs (i.e., modified nucleotides) discussed herein.

In some embodiments, a polynucleotide is provided that comprises a region that is at least 90%, at least 95%, or 100% identical to, or at least 90%, at least 95%, or 100% complementary to, at least 8, at least 9, at least 10, at least 11, at least 12, at least 13, at least 14, at least 15, at least 16, at least 17, at least 18, at least 19, at least 20, at elast 21, at least 22, at least 23, at least 24, at least 25, at least 26, at least 27, at least 28, at least 29, or at least 30 contiguous nucleotides of the TV 40S ribosomal protein (Tv40Srp) gene. In some embodiments, a polynucleotide is provided that comprises a region that is at least 90%, at least 95%, or 100% identical to, or complementary to, a span of 6 to 100, 8 to 100, 8 to 75, 8 to 50, 8 to 40, or 8 to 30 contiguous nucleotides of the TV 40S ribosomal protein (Tv40Srp) gene. Nonlimiting exemplary polynucleotides are shown in Table 1.

In various embodiments, a polynucleotide comprises fewer than 500, fewer than 300, fewer than 200, fewer than 150, fewer than 100, fewer than 75, fewer than 50, fewer than 40, or fewer than 30 nucleotides. In various embodiments, a polynucleotide is between 6 and 200, between 8 and 200, between 8 and 150, between 8 and 100, between 8 and 75, between 8 and 50, between 8 and 40, between 8 and 30, between 15 and 100, between 15 and 75, between 15 and 50, between 15 and 40, or between 15 and 30 nucleotides long.

In some embodiments, the polynucleotide is a primer. In some embodiments, the primer is labeled with a detectable moiety. In some embodiments, a primer is not labeled. A primer, as used herein, is a polynucleotide that is capable of selectively hybridizing to a target gene or to an amplicon that has been amplified from a target gene (collectively referred to as "template"), and, in the presence of the template, a polymerase and suitable buffers and reagents, can be extended to form a primer extension product.

In some embodiments, the polynucleotide is a probe. In some embodiments, the probe is labeled with a detectable moiety. A detectable moiety, as used herein, includes both directly detectable moieties, such as fluorescent dyes, and indirectly detectable moieties, such as members of binding pairs. When the detectable moiety is a member of a binding pair, in some embodiments, the probe can be detectable by incubating the probe with a detectable label bound to the second member of the binding pair. In some embodiments, a probe is not labeled, such as when a probe is a capture probe, e.g., on a microarray or bead. In some embodiments, a probe is not extendable, e.g., by a polymerase. In other embodiments, a probe is extendable.

In some embodiments, the polynucleotide is a FRET probe that in some embodiments is labeled at the 5'-end with a fluorescent dye (donor) and at the 3'-end with a quencher (acceptor), a chemical group that absorbs (i.e., suppresses) fluorescence emission from the dye when the groups are in close proximity (i.e., attached to the same probe). Thus, in some embodiments, the emission spectrum of the dye should overlap considerably with the absorption spectrum of the quencher. In other embodiments, the dye and quencher are not at the ends of the FRET probe.

4.2.7.1. Exemplary Polynucleotide Modifications

In some embodiments, the methods of detecting at least one target gene described herein employ one or more polynucleotides that have been modified, such as polynucleotides comprising one or more affinity-enhancing nucleotide analogs. Modified polynucleotides useful in the methods described herein include primers for reverse transcription, PCR amplification primers, and probes. In some embodiments, the incorporation of affinity-enhancing nucleotides increases the binding affinity and specificity of a polynucleotide for its target nucleic acid as compared to polynucleotides that contain only deoxyribonucleotides, and allows for the use of shorter polynucleotides or for shorter regions of complementarity between the polynucleotide and the target nucleic acid.

In some embodiments, affinity-enhancing nucleotide analogs include nucleotides comprising one or more base modifications, sugar modifications and/or backbone modifications.

In some embodiments, modified bases for use in affinity-enhancing nucleotide analogs include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In some embodiments, affinity-enhancing nucleotide analogs include nucleotides having modified sugars such as 2'-substituted sugars, such as 2'-O-alkyl-ribose sugars, 2'-amino-deoxyribose sugars, 2'-fluoro-deoxyribose sugars, 2'-fluoro-arabinose sugars, and 2'-O-methoxyethyl-ribose (2'MOE) sugars. In some embodiments, modified sugars are arabinose sugars, or d-arabino-hexitol sugars.

In some embodiments, affinity-enhancing nucleotide analogs include backbone modifications such as the use of peptide nucleic acids (PNA; e.g., an oligomer including nucleobases linked together by an amino acid backbone). Other backbone modifications include phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some embodiments, a polynucleotide includes at least one affinity-enhancing nucleotide analog that has a modified base, at least nucleotide (which may be the same nucleotide) that has a modified sugar, and/or at least one internucleotide linkage that is non-naturally occurring.

In some embodiments, an affinity-enhancing nucleotide analog contains a locked nucleic acid ("LNA") sugar, which is a bicyclic sugar. In some embodiments, a polynucleotide for use in the methods described herein comprises one or more nucleotides having an LNA sugar. In some embodiments, a polynucleotide contains one or more regions consisting of nucleotides with LNA sugars. In other embodiments, a polynucleotide contains nucleotides with LNA sugars interspersed with deoxyribonucleotides. See, e.g., Frieden, M. et al. (2008) Curr. Pharm. Des. 14(11):1138-1142.

4.2.7.2. Exemplary Primers

In some embodiments, a primer is provided. In some embodiments, a primer is at least 90%, at least 95%, or 100% identical to, or at least 90%, at least 95%, or 100% complementary to, at least 8, at least 9, at least 10, at least 11, at least 12, at least 13, at least 14, at least 15, at least 16, at least 17, at least 18, at least 19, at least 20, at elast 21, at least 22, at least 23, at least 24, at least 25, at least 26, at least 27, at least 28, at least 29, or at least 30 contiguous nucleotides of the TV 40S ribosomal protein (Tv40Srp) gene. In some embodiments, a primer is provided that comprises a region that is at least 90%, at least 95%, or 100% identical to, or complementary to, a span of 6 to 100, 8 to 100, 8 to 75, 8 to 50, 8 to 40, or 8 to 30 contiguous nucleotides of the TV 40S ribosomal protein (Tv40Srp) gene. Nonlimiting exemplary primers are shown in Table 1. In some embodiments, a primer may also comprise portions or regions that are not identical or complementary to the target gene. In some embodiments, a region of a primer that is at least 90%, at least 95%, or 100% identical or complementary to a target gene is contiguous, such that any region of a primer that is not identical or complementary to the target gene does not disrupt the identical or complementary region.

In some embodiments, a primer comprises a portion that is at least 90%, at least 95%, or 100% identical to a region of a target gene. In some such embodiments, a primer that comprises a region that is at least 90%, at least 95%, or 100% identical to a region of the target gene is capable of selectively hybridizing to an amplicon that has been produced by amplification of the target gene. In some embodiments, the primer is complementary to a sufficient portion of the amplicon such that it selectively hybridizes to the amplicon under the conditions of the particular assay being used.

As used herein, "selectively hybridize" means that a polynucleotide, such as a primer or probe, will hybridize to a particular nucleic acid in a sample with at least 5-fold greater affinity than it will hybridize to another nucleic acid present in the same sample that has a different nucleotide sequence in the hybridizing region. Exemplary hybridization conditions are discussed herein, for example, in the context of a reverse transcription reaction or a PCR amplification reaction. In some embodiments, a polynucleotide will hybridize to a particular nucleic acid in a sample with at least 10-fold greater affinity than it will hybridize to another nucleic acid present in the same sample that has a different nucleotide sequence in the hybridizing region.

In some embodiments, a primer comprises a detectable moiety.

In some embodiments, primer pairs are provided. Such primer pairs are designed to amplify a portion of a target gene, such as the TV 40S ribosomal protein (Tv40Srp) gene, or an endogenous control such as a sample adequacy control (SAC), or an exogenous control such as a sample processing control (SPC). In some embodiments, a primer pair is designed to produce an amplicon that is 50 to 1500 nucleotides long, 50 to 1000 nucleotides long, 50 to 750 nucleotides long, 50 to 500 nucleotides long, 50 to 400 nucleotides long, 50 to 300 nucleotides long, 50 to 200 nucleotides long, 50 to 150 nucleotides long, 100 to 300 nucleotides long, 100 to 200 nucleotides long, or 100 to 150 nucleotides long. Nonlimiting exemplary primer pairs are shown in Table 1.

4.2.7.3. Exemplary Probes

In various embodiments, methods of detecting the presence of *Trichomonas vaginalis* comprise hybridizing nucleic acids of a sample with a probe. In some embodiments, the probe comprises a portion that is complementary to a target gene, such as the TV 40S ribosomal protein (Tv40Srp) gene, or an endogenous control such as a sample adequacy control (SAC), or an exogenous control such as a sample processing control (SPC). In some embodiments, the probe comprises a portion that is at least 90%, at least 95%, or 100% identical to a region of the target gene. In some such embodiments, a probe that is at least 90%, at least 95%, or 100% complementary to a target gene is complementary to a sufficient portion of the target gene such that it selectively hybridizes to the target gene under the conditions of the particular assay being used. In some embodiments, a probe that is complementary to a target gene comprises a region that is at least 90%, at least 95%, or 100% complementary to at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the target gene. Nonlimiting exemplary probes are shown in Table 1. A probe that is at least 90%, at least 95%, or 100% complementary to a target gene may also comprise portions or regions that are not complementary to the target gene. In some embodiments, a region of a probe that is at least 90%, at least 95%, or 100% complementary to a target gene is contiguous, such that any region of a probe that is not complementary to the target gene does not disrupt the complementary region.

In some embodiments, the probe comprises a portion that is at least 90%, at least 95%, or 100% identical to a region of the target gene, such as the TV 40S ribosomal protein (Tv40Srp) gene, or an endogenous control such as a sample adequacy control (SAC), or an exogenous control such as a sample processing control (SPC). In some such embodiments, a probe that comprises a region that is at least 90%, at least 95%, or 100% identical to a region of the target gene is capable of selectively hybridizing to an amplicon that has been produced by amplification of the target gene. In some embodiments, the probe is at least 90%, at least 95%, or 100% complementary to a sufficient portion of the amplicon such that it selectively hybridizes to the amplicon under the conditions of the particular assay being used. In some embodiments, a probe that is complementary to a amplicon comprises a region that is at least 90%, at least 95%, or 100% complementary to at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the amplicon. A probe that is at least 90%, at least 95%, or 100% complementary to an amplicon may also comprise portions or regions that are not complementary to the amplicon. In some embodiments, a region of a probe that is at least 90%, at least 95%, or 100% complementary to an amplicon is contiguous, such that any region of a probe that is not complementary to the amplicon does not disrupt the complementary region.

In some embodiments, the method of detecting one or more target genes comprises: (a) amplifying a region of the target gene; and (b) detecting the amplified region using real time PCR and a detection probe (which may be simultaneous with the amplification step (a)).

As described above, in some embodiments, real time PCR detection may be performed using a FRET probe, which includes, but is not limited to, a TaqMan® probe, a Molecular beacon probe and a Scorpion probe. In some embodiments, the real time PCR detection is performed with a TaqMan® probe, i.e., a linear probe that typically has a fluorescent dye covalently bound at one end of the DNA and a quencher molecule covalently bound elsewhere, such as at the other end of, the DNA. The FRET probe comprises a sequence that is complementary to a region of the amplicon such that, when the FRET probe is hybridized to the amplicon, the dye fluorescence is quenched, and when the probe is digested during amplification of the amplicon, the dye is released from the probe and produces a fluorescence signal. In some embodiments, the amount of target gene in the sample is proportional to the amount of fluorescence measured during amplification.

The TaqMan® probe typically comprises a region of contiguous nucleotides having a sequence that is at least 90%, at least 95%, or 100% identical or complementary to a region of a target gene such that the probe is selectively hybridizable to a PCR amplicon of a region of the target gene. In some embodiments, the probe comprises a region of at least 6 contiguous nucleotides having a sequence that is fully complementary to or identically present in a region of a target gene. In some embodiments, the probe comprises a region that is at least 90%, at least 95%, or 100% identical or complementary to at least 8 contiguous nucleotides, at least 10 contiguous nucleotides, at least 12 contiguous nucleotides, at least 14 contiguous nucleotides, or at least 16 contiguous nucleotides of a target gene to be detected.

In some embodiments, the region of the amplicon that has a sequence that is at least 90%, at least 95%, or 100% complementary to the TaqMan® probe sequence is at or near the center of the amplicon molecule. In some embodiments, there are independently at least 2 nucleotides, such as at least 3 nucleotides, such as at least 4 nucleotides, such as at least 5 nucleotides of the amplicon at the 5'-end and at the 3'-end of the region of complementarity.

In some embodiments, Molecular Beacons can be used to detect PCR products. Like TaqMan® probes, Molecular Beacons use FRET to detect a PCR product via a probe having a fluorescent dye and a quencher attached at the ends of the probe. Unlike TaqMan® probes, Molecular Beacons remain intact during the PCR cycles. Molecular Beacon probes form a stem-loop structure when free in solution, thereby allowing the dye and quencher to be in close enough proximity to cause fluorescence quenching. When the Molecular Beacon hybridizes to a target, the stem-loop structure is abolished so that the dye and the quencher become separated in space and the dye fluoresces. Molecular Beacons are available, e.g., from Gene Link™ (see www.genelink.com/newsite/products/mbintro.asp).

In some embodiments, Scorpion probes can be used as both sequence-specific primers and for PCR product detection. Like Molecular Beacons, Scorpion probes form a stem-loop structure when not hybridized to a target nucleic acid. However, unlike Molecular Beacons, a Scorpion probe achieves both sequence-specific priming and PCR product detection. A fluorescent dye molecule is attached to the 5'-end of the Scorpion probe, and a quencher is attached elsewhere, such as to the 3'-end. The 3' portion of the probe is complementary to the extension product of the PCR primer, and this complementary portion is linked to the 5'-end of the probe by a non-amplifiable moiety. After the Scorpion primer is extended, the target-specific sequence of the probe binds to its complement within the extended amplicon, thus opening up the stem-loop structure and allowing the dye on the 5'-end to fluoresce and generate a signal. Scorpion probes are available from, e.g., Premier Biosoft International (see www.premierbiosoft.com/tech_notes/Scorpion.html).

In some embodiments, labels that can be used on the FRET probes include colorimetric and fluorescent dyes such as Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Examples of dye/quencher pairs (i.e., donor/acceptor pairs) include, but are not limited to, fluorescein/tetramethylrhodamine; IAEDANS/fluorescein; EDANS/dabcyl; fluorescein/fluorescein; BODIPY FL/BODIPY FL; fluorescein/QSY 7 or QSY 9 dyes. When the donor and acceptor are the same, FRET may be detected, in some embodiments, by fluorescence depolarization. Certain specific examples of dye/quencher pairs (i.e., donor/acceptor pairs) include, but are not limited to, Alexa Fluor 350/Alexa Fluor488; Alexa Fluor 488/Alexa Fluor 546; Alexa Fluor 488/Alexa Fluor 555; Alexa Fluor 488/Alexa Fluor 568; Alexa Fluor 488/Alexa Fluor 594; Alexa Fluor 488/Alexa Fluor 647; Alexa Fluor 546/Alexa Fluor 568; Alexa Fluor 546/Alexa Fluor 594; Alexa Fluor 546/Alexa Fluor 647; Alexa Fluor 555/Alexa Fluor 594; Alexa Fluor 555/Alexa Fluor 647; Alexa Fluor 568/Alexa Fluor 647; Alexa Fluor 594/Alexa Fluor 647; Alexa Fluor 350/QSY35; Alexa Fluor 350/dabcyl; Alexa Fluor 488/QSY 35; Alexa Fluor 488/dabcyl; Alexa Fluor 488/QSY 7 or QSY 9; Alexa Fluor 555/QSY 7 or QSY9; Alexa Fluor 568/QSY 7 or QSY 9; Alexa Fluor 568/QSY 21; Alexa Fluor 594/QSY 21; and Alexa Fluor 647/QSY 21. In some instances, the same quencher may be used for multiple dyes, for example, a broad spectrum quencher, such as an Iowa Black® quencher (Integrated DNA Technologies, Coralville, Iowa) or a Black Hole Quencher™ (BHQ™; Sigma-Aldrich, St. Louis, Mo.).

In some embodiments, for example, in a multiplex reaction in which two or more moieties (such as amplicons) are detected simultaneously, each probe comprises a detectably different dye such that the dyes may be distinguished when detected simultaneously in the same reaction. One skilled in the art can select a set of detectably different dyes for use in a multiplex reaction.

Specific examples of fluorescently labeled ribonucleotides useful in the preparation of PCR probes for use in some embodiments of the methods described herein are available from Molecular Probes (Invitrogen), and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences (GE Healthcare), such as Cy3-UTP and Cy5-UTP.

Examples of fluorescently labeled deoxyribonucleotides useful in the preparation of PCR probes for use in the methods described herein include Dinitrophenyl (DNP)-1'-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. Fluorescently labeled nucleotides are commercially available and can be purchased from, e.g., Invitrogen.

In some embodiments, dyes and other moieties, such as quenchers, are introduced into polynucleotide used in the methods described herein, such as FRET probes, via modified nucleotides. A "modified nucleotide" refers to a nucleotide that has been chemically modified, but still functions as a nucleotide. In some embodiments, the modified nucleotide has a chemical moiety, such as a dye or quencher, covalently attached, and can be introduced into a polynucleotide, for example, by way of solid phase synthesis of the polynucleotide. In other embodiments, the modified nucleotide includes one or more reactive groups that can react with a dye or quencher before, during, or after incorporation of the modified nucleotide into the nucleic acid. In specific embodiments, the modified nucleotide is an amine-modified nucleotide, i.e., a nucleotide that has been modified to have a reactive amine group. In some embodiments, the modified nucleotide comprises a modified base moiety, such as uridine, adenosine, guanosine, and/or cytosine. In specific embodiments, the amine-modified nucleotide is selected from 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP. In some embodiments, nucleotides with different nucleobase moieties are similarly modified, for example, 5-(3-aminoallyl)-GTP instead of 5-(3-aminoallyl)-UTP. Many amine modified nucleotides are commercially available from, e.g., Applied Biosystems, Sigma, Jena Bioscience and TriLink.

Exemplary detectable moieties also include, but are not limited to, members of binding pairs. In some such embodiments, a first member of a binding pair is linked to a polynucleotide. The second member of the binding pair is linked to a detectable label, such as a fluorescent label. When the polynucleotide linked to the first member of the binding pair is incubated with the second member of the binding pair linked to the detectable label, the first and second members of the binding pair associate and the polynucleotide can be detected. Exemplary binding pairs include, but are not limited to, biotin and streptavidin, antibodies and antigens, etc.

In some embodiments, multiple target genes are detected in a single multiplex reaction. In some such embodiments, each probe that is targeted to a unique amplicon is spectrally distinguishable when released from the probe, in which case each target gene is detected by a unique fluorescence signal. In some embodiments, two or more target genes are detected using the same fluorescent signal, in which case detection of that signal indicates the presence of either of the target genes or both.

One skilled in the art can select a suitable detection method for a selected assay, e.g., a real-time PCR assay. The selected detection method need not be a method described above, and may be any method.

4.3. Exemplary Compositions and Kits

In another aspect, compositions are provided. In some embodiments, compositions are provided for use in the methods described herein.

In some embodiments, compositions are provided that comprise at least one target gene-specific primer. The term "target gene-specific primer" encompasses primers that have a region of contiguous nucleotides having a sequence that is (i) at least 90%, at least 95%, or 100% identical to a region of a target gene, or (ii) at least 90%, at least 95%, or 100% complementary to the sequence of a region of contiguous nucleotides found in a target gene. In some embodiments, a composition is provided that comprises at least one pair of target gene-specific primers. The term "pair of target gene-specific primers" encompasses pairs of primers that are suitable for amplifying a defined region of a target gene. A pair of target gene-specific primers typically comprises a first primer that comprises a sequence that is at least 90%, at least 95%, or 100% identical to the sequence of a region of a target gene and a second primer that comprises a sequence that is at least 90%, at least 95%, or 100% complementary to a region of a target gene. A pair of primers is typically suitable for amplifying a region of a target gene that is 50 to 1500 nucleotides long, 50 to 1000 nucleotides long, 50 to 750 nucleotides long, 50 to 500 nucleotides long, 50 to 400 nucleotides long, 50 to 300 nucleotides long, 50 to 200 nucleotides long, 50 to 150 nucleotides long, 100 to 300 nucleotides long, 100 to 200 nucleotides long, or 100 to 150 nucleotides long. Nonlimiting exemplary primers, and pairs of primers, are shown in Table 1.

In some embodiments, a composition comprises at least one pair of target gene-specific primers. In some embodiments, a composition additionally comprises a pair of target gene-specific primers for amplifying an endogenous control (such as an SAC) and/or one pair of target gene-specific primers for amplifying an exogenous control (such as an SPC).

In some embodiments, a composition comprises at least one target gene-specific probe. The term "target gene-specific probe" encompasses probes that have a region of contiguous nucleotides having a sequence that is (i) at least 90%, at least 95%, or 100% identical to a region of a target gene, or (ii) at least 90%, at least 95%, or 100% complementary to the sequence of a region of contiguous nucleotides found in a target gene. Nonlimiting exemplary target-specific probes are shown in Table 1.

In some embodiments, a composition (including a composition described above that comprises one or more pairs of target gene-specific primers) comprises one or more probes for detecting the target genes. In some embodiments, a composition comprises a probe for detecting an endogenous control (such as an SAC) and/or a probe for detecting an exogenous control (such as an SPC).

In some embodiments, a composition is an aqueous composition. In some embodiments, the aqueous composition comprises a buffering component, such as phosphate, tris, HEPES, etc., and/or additional components, as discussed below. In some embodiments, a composition is dry, for example, lyophilized, and suitable for reconstitution by addition of fluid. A dry composition may include one or more buffering components and/or additional components.

In some embodiments, a composition further comprises one or more additional components. Additional components include, but are not limited to, salts, such as NaCl, KCl, and $MgCl_2$; polymerases, including thermostable polymerases such as Taq; dNTPs; bovine serum albumin (BSA) and the like; reducing agents, such as β-mercaptoethanol; EDTA and the like; etc. One skilled in the art can select suitable composition components depending on the intended use of the composition.

In some embodiments, compositions are provided that comprise at least one polynucleotide for detecting at least one target gene. In some embodiments, the polynucleotide is used as a primer for a reverse transcriptase reaction. In some embodiments, the polynucleotide is used as a primer for amplification. In some embodiments, the polynucleotide is used as a primer for PCR. In some embodiments, the polynucleotide is used as a probe for detecting at least one target gene. In some embodiments, the polynucleotide is detectably labeled. In some embodiments, the polynucleotide is a FRET probe. In some embodiments, the polynucleotide is a TaqMan® probe, a Molecular Beacon, or a Scorpion probe.

In some embodiments, a composition comprises at least one FRET probe having a sequence that is at least 90%, at least 95%, or 100% identical, or at least 90%, at least 95%, or 100% complementary, to a region of, the TV 40S ribosomal protein (Tv40Srp) gene. In some embodiments, a FRET probe is labeled with a donor/acceptor pair such that when the probe is digested during the PCR reaction, it produces a unique fluorescence emission that is associated with a specific target gene. In some embodiments, when a composition comprises multiple FRET probes, each probe is labeled with a different donor/acceptor pair such that when the probe is digested during the PCR reaction, each one produces a unique fluorescence emission that is associated with a specific probe sequence and/or target gene. In some embodiments, the sequence of the FRET probe is complementary to a target region of a target gene. In other embodiments, the FRET probe has a sequence that comprises one or more base mismatches when compared to the sequence of the best-aligned target region of a target gene.

In some embodiments, a composition comprises a FRET probe consisting of at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides, wherein at least a portion of the sequence is at least 90%, at least 95%, or 100% identical, or at least 90%, at least 95%, or 100% complementary, to a region of, the TV 40S ribosomal protein (Tv40Srp) gene. In some embodiments, at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides of the FRET probe are identically present in, or complementary to a region of, the TV 40S ribosomal protein (Tv40Srp) gene. In some embodiments, the FRET probe has a sequence with one, two or three base mismatches when compared to the sequence or complement of the TV 40S ribosomal protein (Tv40Srp) gene.

In some embodiments, a kit comprises a polynucleotide discussed above. In some embodiments, a kit comprises at least one primer and/or probe discussed above. In some embodiments, a kit comprises at least one polymerase, such as a thermostable polymerase. In some embodiments, a kit comprises dNTPs. In some embodiments, kits for use in the real time PCR methods described herein comprise one or more target gene-specific FRET probes and/or one or more primers for amplification of target genes.

In some embodiments, one or more of the primers and/or probes is "linear". A "linear" primer refers to a polynucleotide that is a single stranded molecule, and typically does not comprise a short region of, for example, at least 3, 4 or 5 contiguous nucleotides, which are complementary to another region within the same polynucleotide such that the primer forms an internal duplex. In some embodiments, the primers for use in reverse transcription comprise a region of at least 4, such as at least 5, such as at least 6, such as at least 7 or more contiguous nucleotides at the 3'-end that has a sequence that is complementary to region of at least 4, such as at least 5, such as at least 6, such as at least 7 or more contiguous nucleotides at the 5'-end of a target gene.

In some embodiments, a kit comprises one or more pairs of linear primers (a "forward primer" and a "reverse primer") for amplification of a target gene. Accordingly, in some embodiments, a first primer comprises a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides having a sequence that is at least 90%, at least 95%, or 100% identical to the sequence of a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides at a first location in the target gene. Furthermore, in some embodiments, a second primer comprises a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides having a sequence that is at least 90%, at least 95%, or 100% complementary to the sequence of a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides at a second location in the target gene, such that a PCR reaction using the two primers results in an amplicon extending from the first location of the target gene to the second location of the target gene.

In some embodiments, the kit comprises at least two, at least three, or at least four sets of primers, each of which is for amplification of a different target gene, such as an endogenous control and/or an exogenous control.

In some embodiments, probes and/or primers for use in the compositions described herein comprise deoxyribonucleotides. In some embodiments, probes and/or primers for use in the compositions described herein comprise deoxyribonucleotides and one or more nucleotide analogs, such as LNA analogs or other duplex-stabilizing nucleotide analogs described above. In some embodiments, probes and/or primers for use in the compositions described herein comprise all nucleotide analogs. In some embodiments, the probes and/or primers comprise one or more duplex-stabilizing nucleotide analogs, such as LNA analogs, in the region of complementarity.

In some embodiments, the kits for use in real time PCR methods described herein further comprise reagents for use in the reverse transcription and amplification reactions. In some embodiments, the kits comprise enzymes such as heat stable DNA polymerases, such as Taq polymerase. In some embodiments, the kits further comprise deoxyribonucleotide triphosphates (dNTP) for use in amplification. In further embodiments, the kits comprise buffers optimized for specific hybridization of the probes and primers.

A kit generally includes a package with one or more containers holding the reagents, as one or more separate compositions or, optionally, as an admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits preferably include instructions for carrying out one or more of the methods described herein. Instructions included in kits can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

In some embodiments, the kit can comprise the reagents described above provided in one or more GeneXpert® Sample cartridge(s). These cartridges permit extraction, amplification, and detection to be be carried out within this self-contained "laboratory in a cartridge." (See e.g., U.S. Pat. Nos. 5,958,349, 6,403,037, 6,440,725, 6,783,736, 6,818,185; each of which is herein incorporated by reference in its entirety.) Reagents for measuring genomic copy number level and detecting a pathogen could be provided in separate cartridges within a kit or these reagents (adapted for multiplex detection) could be provide in a single cartridge.

Any of the kits described here can include, in some embodiments, a receptacle for a urine sample and/or a swab for collecting a urethral swab sample, a vaginal swab sample, or an endocervical swab sample.

The following examples are for illustration purposes only, and are not meant to be limiting in any way.

5. EXAMPLES 5.1. Example 1: Detection of *Trichomonas vaginalis*

An assay was designed to detect the gene for the 40S ribosomal protein (Tv40Srp) of *Trichomonas vaginalis* (TV) by PCR, using the primers and probe shown in Table 1. In addition to the TV-specific primers and probe, primers and probe were included to detect a single-copy human gene used as a sample adequacy control (SAC) target. Primers and probe were also included to detect a bacterial gene, which was included in the multiplex reaction as a sample processing control (SPC) target.

TABLE 1

Primer and probe sequences

| oligo name | target | sequence | SEQ ID NO | Amplicon SEQ ID NO |
|---|---|---|---|---|
| TV forward | Tv40Srp gene | GTAACAACCTTGGAGTTCTTCTTAAG | 1 | 5 |
| TV reverse | Tv40Srp gene | ACATCAATCTACAAGACACCACTTGA | 2 | |
| TV probe | Tv40Srp gene | F1-AGTTTGGCTGCTTAGCTTCGAC-Q1 | 3 | |

The final primer and probe compositions of the multiplex assay are shown in Table 2.

TABLE 2

Primer and probe concentrations

| Target | Label | Purpose | Final conc. Forw. Primer | Final conc. Rev primer | Final conc. Probe |
|---|---|---|---|---|---|
| Tv40Srp | F1 | TV detection | 0.3 µM | 0.3 µM | 0.5 µM |
| single-copy human gene | F2 | SAC | 0.35 µM | 0.35 µM | 0.35 µM |
| bacterial gene | F2 | SPC | 0.4 µM | 0.4 µM | 0.2 µM |

F1 and F2 are detectably different dyes that can be detected and distinguished simultaneously in a multiplex reaction. Each probe also comprises a quencher (e.g., Q1, above).

Each reaction contained 42-58 mM KCl, 3.5-5.0 mM $MgCl_2$, 250-350 µM dNTPs, 50 mM Tris, pH 8.6, and 0.01% sodium azide. AptaTaq (0.27-0.37 units/µl; Roche) was used for amplification.

For each sample to be tested, approximately 7 mL of first catch, voided urine was added to 1 mL of buffer, preferably within 2 hours of sample collection. Physician-collected endocervical swabs or self-collected (in a clinical setting) vaginal swabs were immediately placed into 2.5 mL of buffer.

500 µL of buffered urine or swab sample was loaded into a GeneXpert® cartridge for analysis. The sample was mixed with a lysis reagent to release nucleic acids. After lysis, the released nucleic acid from the sample was captured on a DNA-binding substrate. The nucleic acid was eluted from the substrate and used to reconstitute the reagents used for real-time PCR (described above). The reaction cycle used was: 1 minute at 95° C., followed by up to 40 cycles of 5 seconds at 92.5° C., 20 seconds at 68° C. using a GeneXpert® cartridge in a GeneXpert® system.

The results of the assay were interpreted as shown in Table 3. The valid range of Ct values for the TV, SAC, and SPC targets were 9-39.9 Ct.

TABLE 3

Xpert TV assay results and interpretation

| Result | Interpretation |
|---|---|
| TV DETECTED | Trichomonas target DNA is detected. The Trichomonas target has a Ct within the valid range and a fluorescence endpoint above the threshold setting. SPC-Not applicable. SPC is ignored because the Trichomonas target amplification may compete with this control. SAC-Not applicable. SAC is ignored because the Trichomonas target amplification may compete with this control. PCC-PASS. All probe check results pass. |
| TV NOT DETECTED | Trichomonas target DNA is not detected. SPC meets acceptance criteria. Trichomonas target DNA is not detected. SPC-PASS. SPC has a Ct within the valid range and fluorescence endpoint above the threshold setting. SAC-PASS. SAC has a Ct within the valid range and a fluorescence endpoint above the threshold setting. PCC-PASS. All probe check results pass. |
| INVALID | Presence or absence of Trichomonas target DNA cannot be determined. Repeat test according to the instructions in Section 11.2, Retest Procedure. SPC-FAIL. SPC Ct is not within valid range and the fluorescence endpoint is below the threshold setting. SAC-PASS. SAC has a Ct within the valid range and fluorescence endpoint in the above threshold setting. PCC-PASS. all probe check results pass. Or SPC-PASS. SPC has a Ct within the valid range and fluorescence endpoint above the threshold setting. SAC-FAIL. SAC Ct is not within valid range and fluorescence endpoint is below the threshold setting. PCC-PASS. all probe check results pass. Or SPC-FAIL. SPC Ct is not within valid range and fluorescence endpoint is below the threshold setting. SAC-FAIL. SAC Ct is not within valid range and fluorescence endpoint is below the threshold setting. PCC-PASS. All probe check results pass. |

TABLE 3-continued

Xpert TV assay results and interpretation

| Result | Interpretation |
|---|---|
| ERROR | Presence or absence of Trichomonas target DNA cannot be determined. Repeat test according to the instructions in Section 11.2, Retest Procedure. TRICHOMONAS-NO RESULT SPC-NO RESULT SAC-NO RESULT PCC-FAIL.* All or one of the probe check results fail. |
| NO RESULT | Presence or absence of Trichomonas target DNA cannot be determined. Repeat test according to the instructions in Section 11.2, Retest Procedure. A NO RESULT indicates that insufficient data were collected. For example, the operator stopped a test that was in progress or a power failure occurred. TRICHOMONAS-NO RESULT SPC-NO RESULT SAC-NO RESULT PCC-Not Applicable |

*If the probe check passed, the error is caused by the maximum pressure limit exceeding the acceptable range or by a system component failure.

5.2. Example 2: Clinical Performance

Performance characteristics of the Xpert TV Assay were evaluated at 13 institutions in the U.S. Due to the low prevalence of Trichomonas vaginalis and the difficulty in obtaining fresh Trichomonas vaginalis-positive specimens from male subjects, the specimen population for this study was supplemented with contrived male urine specimens.

Subjects included consenting asymptomatic and symptomatic, sexually active males and females seen in locations including, but not limited to: OB/GYN, sexually transmitted disease (STD), teen, public health, and family planning clinics.

The study specimens consisted of prospectively collected male urine, female urine, endocervical swabs, and patient-collected vaginal swabs (collected in a clinical setting). Contrived male urine specimens were included to supplement the male sample size.

The Xpert TV Assay performance was compared to an FDA-cleared in vitro qualitative nucleic acid amplification comparator assay that detects the ribosomal RNA of Trichomonas vaginalis using a transcription-mediated assay (APTIMA® Trichomonas vaginalis assay, GenProbe Hologic, San Diego, USA). Samples with discrepant results between the Xpert TV Assay and the comparator assay were analysed with bi-directional sequencing of a separate repetitive genomic DNA sequence. See Bandea, et al., Jornal of Clinical Microbiology. 2013, 51(4):1298-1300.

Of the Xpert TV Assays runs performed with eligible specimens, 97.3% (5327/5474) of these specimens were successful on the first attempt. The remaining 147 gave indeterminate results on the first attempt (91 ERROR, 44 INVALID and 12 NO RESULT). One hundred nineteen of the 147 specimens yielded valid results after a single retest; 17 of the specimens were indeterminate on the second attempt and 11 specimens were not retested. The overall assay success rate was 99.5% (5446/5474).

Results from the Xpert TV Assay were compared to the comparator assay, with bi-directional sequencing of discrepants. Sensitivity and specificity by gender, specimen type and symptom status are presented in Table 4.

TABLE 4

| | | | | | | | | Prev | Sensitivity % | Specificity % | PPV % | NPV % |
|---|---|---|---|---|---|---|---|---|---|---|---|---|
| Specimen | | Sx Status | n | TP | FP | TN | FN | % | (95 CI) | (95 CI) | (95 CI) | (95 CI) |

Xpert TV assay vs. reference NAAT test plus sequencing

| Specimen | | Sx Status | n | TP | FP | TN | FN | Prev % | Sensitivity % (95 CI) | Specificity % (95 CI) | PPV % (95 CI) | NPV % (95 CI) |
|---|---|---|---|---|---|---|---|---|---|---|---|---|
| Female | PC-VS | Sym | 717 | 63 | 0 | 649 | 5 | 9.4 | 92.6 (83.7-97.6) | 100 (99.4-100) | 100 (94.3-100) | 99.2 (98.1-99.8) |
| | | Asym | 857 | 50 | 0 | 806 | 1 | 6.1 | 98.0 (89.6-100) | 100 (99.5-100) | 100 (92.9-100) | 99.9 (99.3-100) |
| | | All | 1574 | 113 | 0 | 1455 | 6 | 7.6 | 95.0 (89.3-98.1) | 100 (99.7-100) | 100 (96.8-100) | 99.6 (99.1-99.8) |
| | ES | Sym | 714 | 59 | 0 | 651 | 4 | 8.8 | 93.7 (84.5-98.2) | 100 (99.4-100) | 100 (93.9-100) | 99.4 (98.4-99.8) |
| | | Asym | 859 | 49 | 0 | 809 | 1 | 5.8 | 98.0 (89.4-99.9) | 100 (99.5-100) | 100 (92.7-100) | 99.9 (99.3-100) |
| | | All | 1573 | 108 | 0 | 1460 | 5 | 7.2 | 95.6 (90.0-98.5) | 100 (99.7-100) | 100 (96.6-100) | 99.7 (99.2-99.9) |
| | UR | Sym | 713 | 60 | 0 | 651 | 2 | 8.7 | 96.8 (88.8-99.6) | 100 (99.4-100) | 100 (94.0-100) | 99.7 (98.9-100) |
| | | Asym | 856 | 48 | 0 | 806 | 2 | 5.8 | 96.0 (86.3-99.5) | 100 (99.5-100) | 100 (92.6-100) | 99.8 (99.1-100) |
| | | All | 1569 | 108 | 0 | 1457 | 4 | 7.1 | 96.4 (91.1-99.0) | 100 (99.7-100) | 100 (96.6-100) | 99.7 (99.3-99.9) |
| Male | OR | Sym | 125 | 1 | 0 | 124 | 0 | 0.8 | 100 (2.5-100) | 100 (97.1-100) | 100 (2.5-100) | 100 (97.1-100) |
| | | Asym | 411 | 13 | 0 | 398 | 0 | 3.2 | 100 (75.3-100) | 100 (99.1-100) | 100 (75.3-100) | 100 (99.1-100) |
| | | CS | 183 | 62 | 19 | 99 | 3 | NA | 95.4 (87.1-99.0) | 83.9 (76.0-90.0) | NA | NA |
| | | All | 719 | 76 | 19 | 621 | 3 | NA | 96.2 (89.3-99.2) | 97.0 (95.4-98.2) | NA | NA | a. TP = true positive,
FP = false positive,
TN = true negative,
FN = false negative,
PC-VS = patient-collected vaginal swab,
ES = endocervical swab,
CS = contrived specimens,
UR = urine

5.3. Example 3: Limit of Detection

The analytical sensitivity or limit of detection (LoD) of the Xpert TV Assay was assessed using two *Trichomonas vaginalis* strains, one metronidazole susceptible (*T. vaginalis* ATCC® 30001™), and one metronidazole resistant (*T. vaginalis* ATCC® 30238™). Both strains were tested in *T. vaginalis*-negative pooled male urine (MU) mixed with buffer and *T. vaginalis*-negative pooled vaginal swab (VS) in buffer The limit of detection (LoD) was estimated by testing replicates of 20 at a minimum of five concentrations for each strain and sample type over three days. LoDs were estimated by logistic regression. The LoD is defined as the lowest number of cells/mL that can be reproducibly distinguished from negative samples with 95% confidence or the lowest concentration at which 19 of 20 replicates were positive. The study was performed with two different lots of Xpert TV reagents and the claimed LoD for each strain is the higher of the two determinations (Table 5). For swab samples in buffer, the limit of detection is 5 cells/mL. For urine samples in buffer, the limit of detection is 6 cells/mL. The claimed LoDs were verified by analyzing at least 20 replicates diluted to the estimated LoD concentrations.

TABLE 5

Limit of detection of *Trichomonas vaginalis* using Xpert TV

| | LoD Estimates (Logit) (lower and upper 95% confidence intervals) | | Verified LoD | Verification | LoD Claim |
|---|---|---|---|---|---|
| *Trichomonas vaginalis* strain and matrix | Lot 1 | Lot 2 | (cells/mL) | (Positives/20) | (cells/mL) |
| ATCC 30001 in Vaginal Swab | 3.9 (3.0-6.0) | 4.2 (3.3-6.3) | 4.2 | 20/20 | 5 |
| ATCC 30238 in Vaginal Swab | 4.4 (3.5-6.5) | 3.7 (2.9-5.5) | 4.4 | 19/20 | 5 |

TABLE 5-continued

Limit of detection of *Trichomonas vaginalis* using Xpert TV

| *Trichomonas vaginalis* strain and matrix | LoD Estimates (Logit) (lower and upper 95% confidence intervals) Lot 1 | Lot 2 | Verified LoD (cells/mL) | Verification (Positives/20) | LoD Claim (cells/mL) |
|---|---|---|---|---|---|
| ATCC 30001 in Male Urine | 5.8 (4.7-7.9) | 3.2 (2.6-4.8) | 5.8 | 20/20 | 6 |
| ATCC 30238 in Male Urine | 4.9 (4.0-6.6) | 4.3 (3.4-6.2) | 4.9 | 19/20 | 5 |

5.4. Example 4: Assay Reproducibility

A panel of eight specimens with varying concentrations of *Trichomonas vaginalis* was tested on 12 different days by two different operators, at each of three sites (8 specimens×1 times/day×12 days×2 operators×3 sites). Three lots of Xpert TV Assay were used at each of the 3 testing sites. Xpert TV Assays were performed according to the Xpert TV Assay procedure. Results are summarized in Table 6.

The reproducibility of the Xpert TV Assay was also evaluated in terms of the fluorescence signal expressed in Ct values for each target detected. The mean, standard deviation (SD), and coefficient of variation (CV) between-sites, between-lots, between-days, between-operator, and within-assay for each panel member are presented in Table 7.

TABLE 6

Summary of reproducibility results

| | Site 1 | | | Site 2 | | | Site 3 | | | % Total Agreement |
|---|---|---|---|---|---|---|---|---|---|---|
| Sample | Op 1 | Op 2 | Site | Op 1 | Op 2 | Site | Op 1 | Op 2 | Site | by Sample |
| FS-Neg | 100% (24/24) | 100% (24/24) | 100% (48/48) | 100% (24/24) | 100% (24/24) | 100% (48/48) | 100% (24/24) | 100% (24/24) | 100% (48/48) | 100% (144/144) |
| FS-Mod Pos | 100% (24/24) | 100% (24/24) | 100% (48/48) | 100% (24/24) | 100% (24/24) | 100% (48/48) | 100% (24/24) | 100% (24/24) | 100% (48/48) | 100% (144/144) |
| FS-Low Pos | 62.5% (15/24) | 75.0% (18/24) | 68.8% (33/48) | 70.8% (17/24) | 83.3% (20/24) | 77.1% (37/48) | 90.7% (17/24) | 87.5% (21/24) | 79.2% (38/48) | 75.0% (108/144) |
| FS-LoD | 91.7% (22/24) | 100% (24/24) | 95.8% (46/48) | 95.8% (23/24) | 95.8% (23/24) | 95.8% (46/48) | 95.8% (23/24) | 100% (24/24) | 97.9% (47/48) | 96.5% (139/144) |
| UR-Neg | 100% (24/24) | 100% (24/24) | 100% (48/48) | 100% (24/24) | 100% (24/24) | 100% (48/48) | 100% (24/24) | 100% (24/24) | 100% (48/48) | 100% (144/144) |
| UR-Mod Pos | 100% (24/24) | 100% (24/24) | 100% (48/48) | 100% (24/24) | 100% (24/24) | 100% (48/48) | 100% (24/24) | 100% (24/24) | 100% (48/48) | 100% (144/144) |
| UR-Low Pos | 87.5% (31/24) | 45.8% (11/24) | 66.7% (32/48) | 70.8% (17/24) | 70.8% (17/24) | 70.8% (34/48) | 79.2% (19/24) | 66.7% (16/24) | 72.9% (35/48) | 70.1% (101/144) |
| UR-LoD | 91.7% (22/24) | 100% (24/24) | 95.8% (46/48) | 95.8% (23/24) | 91.7% (22/24) | 93.8% (45/48) | 100% (24/24) | 91.7% (22/24) | 95.8% (46/48) | 95.1% (137/144) | a. FS = female swab matrix;
UR = male urine matrix

TABLE 7

Summary of reproducibility data

| Sample | Assay Channel (Analyte) | $N^a$ | Mean Ct | Between-Site SD | CV (%) | Between-Lot SD | CV (%) | Between-Day SD | CV (%) | Between-Operator SD | CV (%) | Within-Assay SD | CV (%) | Total SD | CV (%) |
|---|---|---|---|---|---|---|---|---|---|---|---|---|---|---|---|
| FS-Neg | SAC | 144 | 24.61 | 0 | 0 | 0.12 | 0.5 | 0.15 | 0.6 | 0 | 0 | 0.31 | 1.3 | 0.37 | 1.5 |
| FS-Mod Pos | TV | 144 | 35.40 | 0.09 | 0.2 | 0.32 | 0.9 | 0.16 | 0.4 | 0 | 0 | 0.68 | 1.9 | 0.77 | 2.2 |
| FS-Low Pos | TV | 108 | 38.18 | 0 | 0 | 0 | 0 | 0 | 0 | 0.52 | 1.4 | 0.86 | 2.3 | 1.01 | 2.6 |
| FS-LoD | TV | 139 | 37.14 | 0.16 | 0.4 | 0.36 | 1.0 | 0.21 | 0.6 | 0 | 0 | 0.92 | 2.5 | 1.02 | 2.7 |
| UR-Neg | SAC | 144 | 34.10 | 0.06 | 0.2 | 0.20 | 0.6 | 0 | 0 | 0.17 | 0.5 | 0.28 | 0.8 | 0.39 | 1.1 |
| UR-Mod Pos | TV | 144 | 35.40 | 0 | 0 | 0.37 | 1.0 | 0.13 | 0.4 | 0.18 | 0.5 | 0.65 | 1.8 | 0.78 | 2.2 |

TABLE 7-continued

Summary of reproducibility data

| Sample | Assay Channel (Analyte) | $N^a$ | Mean Ct | Between-Site | | Between-Lot | | Between-Day | | Between-Operator | | Within-Assay | | Total | |
|---|---|---|---|---|---|---|---|---|---|---|---|---|---|---|---|---|
| | | | | SD | CV (%) | SD | CV (%) | SD | CV (%) | SD | CV (%) | SD | CV (%) | SD | CV (%) |
| UR-Low Pos | TV | 101 | 37.95 | 0 | 0 | 0 | 0 | 0.36 | 1.0 | 0.52 | 1.4 | 0.94 | 2.5 | 1.14 | 3.0 |
| UR-LoD | TV | 137 | 37.03 | 0 | 0 | 0.33 | 0.9 | 0 | 0 | 0 | 0 | 0.96 | 2.6 | 1.01 | 2.7 |

$^a$Results with non-zero Ct valuee out of 144

5.5. Example 5: Analytical Inclusivity

The analytical inclusivity of the Xpert TV Assay was evaluated by testing 17 *T. vaginalis* strains in triplicate at a concentration no greater than 3× analytical limit of detection (3×LoD). Strains were tested in *T. vaginalis*-negative pooled vaginal swab (VS) in buffer, and male urine (MU) mixed with buffer. See Table 8. Under the conditions of this study, all strains reported TV DETECTED results. The Xpert TV assay demonstrated 100% inclusivity in both sample types.

TABLE 8

Analytical inclusivity panel

| Isolate ATCC # | Isolation Source | Results Vaginal Swab | Results Male Urine |
|---|---|---|---|
| 30001 | Vaginal exudate | TV DETECTED | TV DETECTED |
| 30184 | Vaginal swab | TV DETECTED | TV DETECTED |
| 30187 | Endocervical swab | TV DETECTED | TV DETECTED |
| 30188 | Vagina | TV DETECTED | TV DETECTED |
| 30236 | Endocervical swab | TV DETECTED | TV DETECTED |
| 30240 | Vaginal pool | TV DETECTED | TV DETECTED |
| 30245 | Vaginal and Endocervical material | TV DETECTED | TV DETECTED |
| 30247 | Vagina | TV DETECTED | TV DETECTED |
| 50138 | human | TV DETECTED | TV DETECTED |
| 50139 | human | TV DETECTED | TV DETECTED |
| 50141 | human | TV DETECTED | TV DETECTED |
| 50143 | human | TV DETECTED | TV DETECTED |
| 50147 | human | TV DETECTED | TV DETECTED |
| 50167 | Vagina | TV DETECTED | TV DETECTED |
| 50183 | Prostatic fluid | TV DETECTED | TV DETECTED |
| PRA-95 | Vaginal exudate | TV DETECTED | TV DETECTED |
| PRA-98 | human | TV DETECTED | TV DETECTED |

5.6. Example 6: Analytical Specificity

A panel of 47 organisms, including bacteria, fungi, and viruses commonly found in the urogenital tract, as well as other closely related protozoans to *Trichomonas* were tested with the Xpert TV Assay. Each bacterial or fungal strain was tested at 1×10$^7$ cfu/mL or greater. Strains which did not produce countable colonies were diluted to 0.5 McFarland units, approximately equivalent to 1.5×108 cfu per mL for *E. coli*. Viral strains were purchased as heat inactivated stocks from ZeptoMetrix Corp. and tested at 1×10$^6$ U/mL or 10$^6$ genomes/mL. Protozoans were cultured in growth media, visually enumerated by light microscopy and tested at 1×10$^6$ cells/mL. Tests were performed in triplicate. The organisms tested and the Xpert TV assay results are listed in Table 9.

One organism, *Trichomonas tenax*, reported a TV DETECTED result with the Xpert TV assay. Under the conditions of this study, the analytical specificity of the Xpert TV Assay was 98%.

TABLE 9

Analytical specificity panel

| Species | Strain ID | Test Result |
|---|---|---|
| *Acinetobacter Iwoffi* | ATCC 17925 | TV NOT DETECTED |
| *Actinomyces israelii* | ATCC 12102 | TV NOT DETECTED |
| *Atopobium vaginae* | ATCC BAA-55 | TV NOT DETECTED |
| *Bacteroides fragilis* | ATCC 25285 | TV NOT DETECTED |
| *Bacteroides ureolyticus* | ATCC 33387 | TV NOT DETECTED |
| *Bifidobacterium adolescentis* | ATCC 15703 | TV NOT DETECTED |
| *Campylobacter jejuni* | ATCC 33560 | TV NOT DETECTED |
| *Candida albicans* | ATCC 14053 | TV NOT DETECTED |
| *Candida glabrata* | ATCC 90030 | TV NOT DETECTED |
| *Candida parapsilosis* | ATCC 90018 | TV NOT DETECTED |
| *Candida tropicalis* | ATCC 13803 | TV NOT DETECTED |
| *Chlamydia trachomatis* | ATCC VR-885 | TV NOT DETECTED |
| *Clostridium difficile* | ATCC 43594 | TV NOT DETECTED |
| *Clostridium perfringens* | ATCC 13124 | TV NOT DETECTED |
| *Corynebacterium genitalium* | ATCC 33031 | TV NOT DETECTED |
| *Cryptococcus neoformans* | ATCC 32045 | TV NOT DETECTED |
| Cytomegalovirus | ZeptoMetrix 0810003CF | TV NOT DETECTED |
| *Enterobacter aerogenes* | ATCC 51697 | TV NOT DETECTED |
| *Enterococcus feacalis* | ATCC 19433 | TV NOT DETECTED |
| *Escherichia coil* | ATCC 24922 | TV NOT DETECTED |
| *Fusobacterium nucleatum* | ATCC 31647 | TV NOT DETECTED |
| *Gardnerella vaginalis* | ATCC 49145 | TV NOT DETECTED |
| *Haemophilus ducreyi* | ATCC 33940 | TV NOT DETECTED |
| Herpes simplex virus I | ZeptoMetrix 0810005CF | TV NOT DETECTED |
| Herpes simplex virus II | ZeptoMetrix 0810006CF | TV NOT DETECTED |
| HIV-1 | ZeptoMetrix 0801032CF | TV NOT DETECTED |
| HPV 16 (Caski) | ZeptoMetrix 0810232 | TV NOT DETECTED |
| *Klebsiella oxytoca* | ATCC 43165 | TV NOT DETECTED |
| *Lactobacillus acidophilus* | ATCC 314 | TV NOT DETECTED |
| *Lactobacillus jensenii* | ATCC 25258 | TV NOT DETECTED |
| *Lactobacillus vaginalis* | ATCC 49540 | TV NOT DETECTED |
| *Listeria monocytogenes* | ATCC 15313 | TV NOT DETECTED |
| *Mobiluncus curtisil* | ATCC 35241 | TV NOT DETECTED |
| *Mycoplasma hominis* | ATCC 23114 | TV NOT DETECTED |
| *Neisseria gonorrhoeae* | ATCC 35201 | TV NOT DETECTED |
| *Pentatrichomonas hominis* | ATCC 30000 | TV NOT DETECTED |
| *Peptostreptococcus anaerobius* | ATCC 49031 | TV NOT DETECTED |
| *Prevotella bivia* | ATCC 29303 | TV NOT DETECTED |
| *Propionibacterium acnes* | ATCC 6919 | TV NOT DETECTED |
| *Proteus mirabilis* | ATCC 25933 | TV NOT DETECTED |
| *Pseudomonas aeruginosa* | ATCC 35554 | TV NOT DETECTED |
| *Staphylococcus aureus* | ATCC 700699 | TV NOT DETECTED |
| *Staphylococcus epidermidis* | ATCC 14990 | TV NOT DETECTED |
| *Streptococcus agalactiae* | ATCC 13813 | TV NOT DETECTED |

TABLE 9-continued

Analytical specificity panel

| Species | Strain ID | Test Result |
|---|---|---|
| Streptococcus pyogenes | ATCC 19615 | TV NOT DETECTED |
| Trichomonas tenax | ATCC 30207 | TV DETECTED |
| Ureaplasma urealyticum | ATCC 27618 | TV NOT DETECTED |

5.7. Example 7: Interfering Substances

In a non-clinical study, potentially interfering endogenous and exogenous substances that may be within the urogenital tract and present in endocervical and vaginal swab or first catch urine samples were evaluated with the Xpert TV Assay.

Substances were individually diluted into a pooled negative vaginal swab matrix and a pooled negative male urine matrix. The substances were also tested in the same matrices spiked with *T. vaginalis* cells at no greater than three times the limit of detection for the respective sample type. Eight replicates of each set of negative and positive samples were tested with the Xpert TV assay and compared to the results obtained in a control of the same sample without the potential interfering substance added. The substances and test concentrations are listed in Table 10 and Table 11.

Under the conditions of the study, in tests with the substances diluted into negative urine matrix no invalid results were reported; all tests reported TV NOT DETECTED as expected. Assay interference was observed in tests with blood at 0.75% v/v and azithromycin at 1.8 mg/mL diluted into positive urine matrix. False negative results were not reported for tests with blood at 0.5% v/v and azithromycin at 1 mg/mL.

Under the conditions of the study, in tests with the substances diluted into pooled negative swab matrix no invalid results were reported; all tests reported TV NOT DETECTED as expected.

In testing of substances diluted into pooled positive swab matrix, no false negative TV results were reported. Testing with all the substances reported TV DETECTED results as expected.

TABLE 10

Potentially interfering substances in urine samples

| Class/Substance | Active Ingredient | Concentration Tested |
|---|---|---|
| Blood | Blood | 0.3% v/v |
| Seminal Fluid | Seminal Fluid | 5.0% v/v |
| Mucus | Mucin | 0.8% w/v |
| Analgesics & Antibiotics | Acetylsalicylic Acid 500 mg | 8 mg/mL |
| | Acetaminophen | 3.2 mg/mL |
| | Azithromycin | 1.0 mg/mL |
| | Doxycycline | 0.5 mg/mL |
| OTC Deodorant & Powders | PEG-20; PEG-32; PEG-20 Stearate | 0.25% w/v |
| | Nanoxynol-9 | 0.25% w/v |
| Albumin | BSA | 10 mg/ml |
| Glucose | Glucose | 10 mg/ml |
| Bilirubin | Bilirubin | 1 mg/ml |

TABLE 10-continued

Potentially interfering substances in urine samples

| Class/Substance | Active Ingredient | Concentration Tested |
|---|---|---|
| Acidic Urine (pH 4.0) | Urine + N-Acetyl-L-Cysteine | pH 4.0 |
| Alkaline Urine (pH 9.0) | Urine + Ammonium Citrate | pH 9.0 |
| Leukocytes | Leukocytes | $10^6$ cells/mL |
| Intravaginal Hormones | Progesterone; Estradiol | 7 mg/mL Progesterone + 0.07 mg/mL Beta Estradiol |

TABLE 11

Potentially interfering substances in swab samples

| Class/Substance | Active Ingredient | Concentration Tested |
|---|---|---|
| Blood | Blood | 1.0% v/v |
| Seminal Fluid | Seminal Fluid | 5.0% v/v |
| Mucus | Mucin | 0.8% w/v |
| Over the counter (OTC) Vaginal Products; Contraceptives; Vaginal treatments | Benzocaine 5%; Resorcinol 2% | 0.25% w/v |
| | Clotrimazole 2% | 0.25% w/v |
| | Miconazole Nitrate 2% | 0.25% w/v |
| | Tioconazole | 0.25% w/v |
| | 5% w/w Aciclovir | 0.25% w/v |
| | Glycerin, Propylene glycol | 0.25% w/v |
| | Glycerin; Carbomer | 0.12% w/v |
| | Glycerin, Hydroxyethyl cellulose | 0.25% w/v |
| | Goldenseal 3X HPUS; Kreosotum 12X HPUS | 0.25% w/v |
| | Povidone-iodine 10% | 0.25% v/v |
| | Nonoxynol-9 12.5% | 0.25% w/v |
| Hemerrhoidal Cream | Glycerin 14%; Pramoxine HCl 1% | 0.25% w/v |
| Leukocytes | Leukocytes | $10^6$ cells/mL |
| Intravaginal Hormones | Progesterone; Estradiol | 7 mg/mL Progesterone + 0.07 mg/mL Beta Estradiol |

5.8. Example 8: Carry-Over Contamination

The study consisted of repeated tests of a TV-negative vaginal swab pool in buffer sample processed within the same GeneXpert module immediately following a high ($10^6$ cells/mL) TV positive vaginal swab pool in buffer sample. The study consisted of a TV-negative vaginal swab pool in buffer sample processed within the same GeneXpert module immediately followed by a high ($10^6$ cells/mL) TV positive vaginal swab pool in buffer sample. This testing scheme was repeated a further 20 times on two GeneXpert modules for a total of 82 runs resulting in 40 positive and 42 negative samples. All 40 positive samples were correctly reported as TV DETECTED and all 42 negative samples were correctly reported as TV NOT DETECTED.

5.9. Example 9: Alternate Primers and Probes Tested to Detect TV

To develop the TV assay described herein, four different forward primer, two different reverse primers, and two different probes for detecting the TV 40S ribosomal protein (Tv40Srp) gene were tested for sensitivity and specificity (e.g., cross-reactivity with other species) in the assay. Table 12 shows the tested primers and probes.

TABLE 12

Alternate primer and probe sequences

| oligo name | SEQ ID NO | sequence | Results |
|---|---|---|---|
| TV forward | 1 | GTAACAACCTTGGAGTTCTTCTTAAG | Final design |
| TV reverse | 2 | ACATCAATCTACAAGACACCACTTGA | Final design |
| TV probe | 3 | F1-AGTTTGGCTGCTTAGCTTCGAC-Q1 | Final design |
| TV forward ALT1 | 6 | GAGTTCTTCTTAAGCTGAACAC | FW design 2 |
| TV forward ALT2 | 7 | GAGTTCTTCTTGAGCTGAACAC | FW design 2 with different SNP at position 12 |
| TV forward ALT3 | 8 | AACAACCTTGGAGTTCTTCTTA | FW design 3 |
| TV reverse ALT1 | 9 | ATCTACAAGACACCACTTGA | RV design 2 |
| TV probe ALT1 | 10 | F1-AGTTTGGCTGCTTGGCTTCGAC-Q1 | PR design 2 with different SNP at position 14 |

It was found that TV forward ALT1 cross-reacted with *Pentatric homonas hominis* (Pth), another closely related trichomonad found in human gut. When TV forward ALT1 was used in an assay with 1000 copies of TV and an assay with 500,000 copies of Pth, TV was detected with a Ct of 30.7 and Pth was detected with a Ct of 26.3. TV forward ALT2 was less sensitive than the final design, detecting TV with a higher Ct value of 31.5. Similarly, TV forward ALT3 was less sensitive than the final design, also detecting TV with a higher Ct value. TV reverse ALT1 also resulted in a less sensitive assay, detecting TV with a higher Ct value. Finally, TV probe ALT1 was less sensitive and less consistent than the final design.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that changes can be made without departing from the spirit and scope of the invention(s).

TABLE OF CERTAIN SEQUENCES

| SEQ ID NO | Description | Sequence |
|---|---|---|
| 4 | *Trichomonas vaginalis* 40S ribosomal protein (Tv40Srp) gene | ggccggcctt tctgatgggt aagtctaaag cttgcggtcg tctcgctgct cgtaaactcc gtcttgcaca caagtccaac ttgtgggctt ccaacgcata ccgccgttcc cttggtacat caatctacaa gacaccactt gagggtacat caatggcatc tggcatcgtc gtcggcaagg tcgctgtcga agccaagcag ccaaactctg ctattcgtaa agctgtccgt gttcagctta agaagaactc taaggttgtc acagctttcg ttccacgcga tggttccctc cgtcttattg atgataacga ccgtgttctt attgccggta tgggtcgttc tggccgttct gtcggtgacc ttccaggatg ccgtttcaaa gttatcaagg tcgctggttt ctccctcctt gctctttggc tcggcaagaa ggagaagccg cgcagctaaa taaatactct tgggtttacc ggtaaataaa aacatatatt acgaaataca aatattat |
| 5 | Tv40Srp amplicon | ACATCAATCT ACAAGACACC ACTTGAAGGC ACCTCAATGG CCTCCGGCAT TGTTGTCGGC AAAGTTGCTG TCGAAGCTAA GCAGCCAAAC TCCGCTATTC GTAAAGCAGT TCGTGTTCAG CTTAAGAAGA ACTCTAAAGT TGTTAC |

What is claimed is:

1. A composition comprising a set of primers and a probe for detecting a *Trichomonas vaginalis* 40S ribosomal protein (Tv40Srp) gene or RNA, wherein the Tv40Srp gene comprises the sequence of SEQ ID NO: 4, and wherein the set of primers comprises a first primer comprising a region of at least 8 contiguous nucleotides having a sequence that is at least 90% identical to a region of at least 8 contiguous nucleotides of SEQ ID NO: 1, SEQ ID NO: 6, SEQ ID NO: 7, or SEQ ID NO: 8; and a second primer comprising a region of at least 8 contiguous nucleotides having a sequence that is at least 90% complementary to a region of at least 8 contiguous nucleotides of SEQ ID NO: 2 or SEQ ID NO: 9; wherein the probe is capable of selectively hybridizing to a Tv40Srp amplicon produced by the first primer and second primer, and wherein the probe comprises a region of at least 8 contiguous nucleotides having a sequence that is at least 90% identical or complementary to a region of at least 8 contiguous nucleotides of SEQ ID NO: 3 or SEQ ID NO: 10 and comprises a detectable label.

2. The composition of claim 1, wherein the first primer comprises a region of at least 8 contiguous nucleotides having a sequence that is identical to a region of at least 8 contiguous nucleotides of SEQ ID NO: 1 and the second primer comprises a region of at least 8 contiguous nucleotides having a sequence that is identical to a region of at least 8 contiguous nucleotides of SEQ ID NO: 2.

3. The composition of claim 1, wherein the probe comprises a region of nucleotides having a sequence that is at least 90%, at least 95%, or 100% identical or complementary to a region of at least 15, at least 16, at least 17, at least 18, at least 19, at least 20, at least 21, or at least 22 contiguous nucleotides of SEQ ID NO: 3 or SEQ ID NO: 10.

4. The composition of claim 1, wherein the probe comprises a region of at least 8 contiguous nucleotides having a sequence that is identical or complementary to a region of at least 8 contiguous nucleotides of SEQ ID NO: 3 or SEQ ID NO: 10.

5. The composition of claim 1, wherein the first primer comprises a region of at least 8 contiguous nucleotides having a sequence that is identical to a region of at least 8 contiguous nucleotides of SEQ ID NO: 1, and the second primer comprises a region of at least 8 contiguous nucleotides having a sequence that is identical to a region of at least 8 contiguous nucleotides of SEQ ID NO: 2, and wherein the probe comprises a region of at least 8 contiguous nucleotides having a sequence that is identical or complementary to a region of at least 8 contiguous nucleotides of SEQ ID NO: 3.

6. The composition of claim 1, wherein the composition is a lyophilized composition or is in solution.

7. A kit comprising a set of primers and a probe for detecting a *Trichomonas vaginalis* 40S ribosomal protein (Tv40Srp) gene or RNA, wherein the Tv40Srp gene comprises the sequence of SEQ ID NO: 4, and wherein the set of primers comprises a first primer comprising a region of at least 8 contiguous nucleotides having a sequence that is at least 90% identical to a region of at least 8 contiguous nucleotides of SEQ ID NO: 1, SEQ ID NO: 6, SEQ ID NO: 7, or SEQ ID NO: 8; and a second primer comprising a region of at least 8 contiguous nucleotides having a sequence that is at least 90% complementary to a region of at least 8 contiguous nucleotides of SEQ ID NO: 2 or SEQ ID NO: 9, wherein the probe is capable of selectively hybridizing to a Tv40Srp amplicon produced by the first primer and second primer, and wherein the probe comprises a region of at least 8 contiguous nucleotides that is at least 90% identical or complementary to a region of at least 8 contiguous nucleotides of SEQ ID NO: 3 or SEQ ID NO: 10 and comprises a detectable label.

8. The kit of claim 7, wherein the kit comprises a primer pair for detecting an endogenous control and/or a primer pair for detecting an exogenous control, wherein the primer pairs for detecting Tv40Srp and the controls are each in the same or different compositions in the kit.

9. The kit of claim 8, wherein the endogenous control is a sample adequacy control.

10. The kit of claim 8, wherein the endogenous control is selected from HMBS, GAPDH, beta actin, and beta globin.

11. The kit of claim 8, wherein the exogenous control is a sample processing control.

12. The kit of claim 8, wherein the exogenous control is a bacterial gene.

13. The kit of claim 7, wherein the first primer comprises a region of at least 8 contiguous nucleotides having a sequence that is identical to a region of at least 8 contiguous nucleotides of SEQ ID NO: 1, and the second primer comprises a region of at least 8 contiguous nucleotides having a sequence that is identical to a region of at least 8 contiguous nucleotides of SEQ ID NO: 2.

14. The kit of claim 8, wherein the kit further comprises a second probe capable of selectively hybridizing to an endogenous control amplicon, and/or a third probe capable of selectively hybridizing to an exogenous control amplicon, wherein the probes are in the same or different composition from one or more of the primer pairs.

15. The kit of claim 7, wherein the probe comprises a region of at least 8 nucleotides that is identical or complementary to a region of at least 8 contiguous nucleotides of SEQ ID NO: 3 or SEQ ID NO: 10.

16. The kit of claim 7, wherein the probe comprises the sequence of SEQ ID NO: 3 or SEQ ID NO: 10.

17. A kit comprising a set of primers and a probe for detecting a *Trichomonas vaginalis* 40S ribosomal protein (Tv40Srp) gene or RNA, wherein the Tv40Srp gene comprises the sequence of SEQ ID NO: 4, and wherein the set of primers comprises a first primer comprising a region of at least 8 contiguous nucleotides having a sequence that is at least 90% identical to a region of at least 8 contiguous nucleotides of SEQ ID NO: 1, SEQ ID NO: 6, SEQ ID NO: 7, or SEQ ID NO: 8; and a second primer comprising a region of at least 8 nucleotides having a sequence that is at least 90% complementary to a region of at least 8 contiguous nucleotides of SEQ ID NO: 2 or SEQ ID NO: 9, wherein the probe is capable of selectively hybridizing to a Tv40Srp amplicon produced by the first primer and second primer, wherein the probe comprises the sequence of SEQ ID NO: 3 or SEQ ID NO: 10 and comprises a detectable label.

18. The composition of claim 1, wherein the first primer comprises the sequence of SEQ ID NO: 1, SEQ ID NO: 6, SEQ ID NO: 7, or SEQ ID NO: 8 and the second primer comprises the sequence of SEQ ID NO: 2 or SEQ ID NO: 9.

19. The composition of claim 1, wherein the first primer comprises the sequence of SEQ ID NO: 1 and the second primer comprises the sequence of SEQ ID NO: 2.

20. The kit of claim 7, wherein the first primer comprises the sequence of SEQ ID NO: 1, SEQ ID NO: 6, SEQ ID NO: 7, or SEQ ID NO: 8 and the second primer comprises the sequence of SEQ ID NO: 2 or SEQ ID NO: 9.

21. The kit of claim 7, wherein the first primer comprises the sequence of SEQ ID NO: 1 and the second primer comprises the sequence of SEQ ID NO: 2.

* * * * *